(12) United States Patent
Royzen

(10) Patent No.: US 8,776,807 B2
(45) Date of Patent: Jul. 15, 2014

(54) DENTAL DEVICE

(76) Inventor: Michael Zinovy Royzen, Seattle, WA (US)

(*) Notice: Subject to any disclaimer, the term of this patent is extended or adjusted under 35 U.S.C. 154(b) by 114 days.

(21) Appl. No.: 13/200,838

(22) Filed: Oct. 4, 2011

(65) Prior Publication Data

US 2013/0081649 A1 Apr. 4, 2013

(51) Int. Cl.
*A61C 15/00* (2006.01)

(52) U.S. Cl.
USPC .......................................... 132/321; 132/329

(58) Field of Classification Search
USPC ............... 132/321, 329; 433/141; 206/368; D28/65
See application file for complete search history.

(56) References Cited

U.S. PATENT DOCUMENTS

| 86,637 | A | * | 2/1869 | Bowser | 24/13 |
|---|---|---|---|---|---|
| 186,952 | A | * | 2/1877 | Poznanski | 132/328 |
| 272,985 | A | * | 2/1883 | Stone | 63/1.12 |
| 1,355,037 | A | * | 10/1920 | Dziuk | 132/328 |
| 2,925,087 | A | * | 2/1960 | Kucher | 132/329 |
| 4,800,905 | A | * | 1/1989 | Stuart | 132/328 |
| 5,975,901 | A | * | 11/1999 | Kennedy | 433/141 |
| 6,848,453 | B2 | * | 2/2005 | Hampton | 132/321 |
| 2008/0104786 | A1 | * | 5/2008 | Hohlbein et al. | 15/167.1 |

* cited by examiner

*Primary Examiner* — Robyn Doan

(57) ABSTRACT

A dental device including a toothpick or a length of dental floss or both of them retains cleaning parts in their containers sanitary and releasably by the user of the device. The device is formed into a closed figure which can be flat or three dimensional. The figure can be changed by the user of the dental device. The device can be placed around another object, for example, a user's wrist or utensils. The device can have decorative elements. The dental device is attractive to young users, safe, user friendly and sanitary to carry.

3 Claims, 28 Drawing Sheets

DENTAL DEVICE

BACKGROUND OF THE INVENTION this invention relates to toothpicks and dental floss for cleaning teeth and removing plaque.

Toothpicks are beneficial dental devices. They are small and easy to carry. However, when they are carried unprotected in the pocket, they become dirty and are not sanitary. Because toothpicks are sharply pointed objects, they could penetrate the user's clothing and could cause discomfort or pain to the user when they engage the adjoining body portion or skin.

According to U.S. Pat. No. 4,040,433 to Edison, U.S. Pat. No. 5,076,301 to Sulskis, U.S. Pat. No. 6,418,940 to Tcherny, toothpicks are enclosed in protective sanitary containers.

According to U.S. Pat. No. 4,800,905 to Stuart, the toothpick case used as a handle. However, after taking out a toothpick from the case, it is necessary to mount the toothpick to the case in order to use the case as a handle.

Known sanitary containers storing more than one toothpick could be easily contaminated during taking out of the container even the very first toothpick, especially, when the user has no possibility to wash his or her hands before doing it. A toothpick which is taken out could be contaminated as well.

There are known combinations of toothpicks and dental floss, for example U.S. Pat. Application No. 2006/0070636 to Peters describes a toothpick with a length of dental floss wound around it. Most of such devices need sanitary cases to protect both toothpick and dental floss.

According to U.S. Pat. No. 5,915,392 to Isaac, the described combination of a toothpick and dental floss holds the floss inside the toothpick. However, the toothpick itself needs a sanitary container. The toothpick has a perforated area or break point near its middle. When the toothpick is broken a useable length of dental floss is exposed, however, the surfaces of the broken ends are not safe especially for children users because they may result in pricking the user's face, his or her mouth or hands.

According to U.S. Pat. No. 5,174,314 to Charatan and to U.S. Pat. No. 4,403,625 to Sanders, the described devices contain floss in housings with pointed ends to be used as toothpicks. However, the housings if they are used as toothpicks need sanitary containers. In order to release the floss, the parts of the housing should be separated. The patents teach to clean teeth with floss attached to parts with pointed ends which is not safe especially for children users because it may result in pricking the user's face or his or her mouth.

Many children were braces in order to correct the position of their teeth. They are recommended to clean their teeth and braces after each meal. However existing toothpicks and toothpick and floss combinations are not safe enough, sanitary and attractive to children users.

SUMMARY OF THE INVENTION

The objective of the present invention is to provide a dental device suitable for safe, convenient and sanitary use. Another objective of the invention is to make a dental device more attractive for children users.

The present invention of a dental device provides a toothpick connected to a sanitary container. The toothpick with an elongated body has from one end a part adapted for cleaning teeth. The elongated container has a longitudinal cavity opened in its first end. The cavity is adapted to receive at least a cleaning part of the toothpick and retain it sanitary and releasably by the user of the device. The other end of the toothpick is connected to the second end of the container. At least a part of the dental device is made bendable, flexible or elastic. The lengths of the parts of the device are adjusted to allow insertion of at least the cleaning part of the toothpick into the cavity and its, removal of by the user of the device and adjustment of the shape of the device for its convenient use. Before use, the cleaning part of the toothpick is retained in the cavity of the container in sanitary conditions. In this state the dental device forms a closed figure with no sharp points. As a result, the device is safe, user friendly and sanitary to carry. In order to clean teeth, the user removes the retaining cleaning member from the cavity and, if necessary, adjusts the shape of the bendable device to make it more convenient for cleaning. Providing the device as a closed figure makes the device more attractive to children users.

In another embodiment, the closed figure formed by the dental device is flat, for example, a circle, D-shaped figure, triangle, square, oval or a three dimensional figure. Providing the different shapes of the dental device makes the device more attractive to children users.

In another embodiment, the dental device has at least one bendable or flexible part adapted to allow the user of the device to change the shape of the device while keeping the cleaning part of the toothpick retained in the cavity of the container. Providing the dental device with shape changeable by the user of the device makes the device more attractive to children users.

In another embodiment, a member connecting the container and the toothpick is tubular.

In another embodiment, the member connecting the container and toothpick and the container is made as a single piece body. The single piece body can be made tubular. As an alternative, the member and the toothpick can be made as a single piece body. The single piece body can be made tubular.

In another embodiment, the whole dental device is made as a single piece body. The single piece body can be made tubular.

In another embodiment, the dental device has a curved container which retains correspondently curved the cleaning part of the toothpick. The cleaning part of the toothpick is adjusted to retain its curved shape after removing it from the curved container. Both curved container and curved toothpick make the dental device more attractive to children users.

In another embodiment, the dental device is adapted to be placed around another object, including a user's wrist, or a drinking cup, or utensils. Placing the dental device around another object, especially, a user's wrist as a wrist band makes the device very attractive to children users. Wearing the dental device as a wrist band makes the device easily available for use when it is needed.

In another embodiment, the dental device is adapted to be attached to an object having a hole.

In another embodiment, the dental device has at least one decorative element. Providing the dental device with a decorative element makes the device more attractive to children users.

In another embodiment, the dental device is comprising two or more teeth cleaning devices. All devices are positioned and aligned in such a way so the cleaning part of each device is inserted into the cavity of the container of the adjusting device forming a closed figure and each cavity retains the inserted cleaning member sanitary and releasably by the user of the device.

In another embodiment, at least a part of at least one of the teeth cleaning devices has a different color.

In another embodiment, the dental device includes a length of dental floss. The cavity of the container is separated into two chambers. The first chamber is adjusted to retain the cleaning part of the toothpick. The second chamber is open at the second end of the container and adjusted for retaining the length of dental floss. One end of the dental floss is affixed to the container inside the second cavity and the other end of the dental floss if affixed to the end of the member connecting the end of the toothpick with the container. This end of the connecting member is adjusted to provide a releasable sealing engagement between it and the second cavity in order to retain the dental floss sanitary and releasably by the user of the device.

In another embodiment, the dental device includes an additional toothpick. The cavity of the container is separated into two chambers. The first chamber is adjusted to retain the cleaning part of the first toothpick. The second chamber is open at the second end of the container and adjusted for retaining the cleaning part of the second toothpick sanitary and releasably by the user of the device, and the second ends of the toothpicks are connected.

In another embodiment, a dental device for cleaning teeth comprising at least two toothpicks, each toothpick has an elongated body having from one end a part adapted for cleaning teeth and an elongated cavity open in its second end, and said cavity is adjusted to retain the cleaning part of a toothpick. All toothpicks are positioned and aligned in such a way so the cleaning part of each device is inserted into the cavity of the adjusting toothpick forming a closed figure and each cavity retains the inserted cleaning part sanitary and releasably by the user of the device.

In another embodiment, a dental device for cleaning teeth comprising at least one toothpick, an elongated container and a length of dental floss. The toothpick has an elongated body having from one end a part adapted for cleaning teeth and an elongated cavity open in its second end. The container has an elongated cavity open at its first end and said cavity is adapted to retain the cleaning part of the toothpick, and a part adjusted for sealing the cavity of the toothpick at its second end. The cleaning part of the toothpick is inserted into the cavity of the container cavity for retaining the inserted cleaning part sanitary and releasably by the user of the device. The sealing part of the connector provides engagement with the end of the toothpick sealing its cavity. One end of the dental floss is affixed to the sealing part of the container and the other end is affixed or not to the toothpick inside its cavity and the dental floss is retained sanitary and releasably by the user of the device inside the cavity of the toothpick. When both the cleaning part of the toothpick and the dental floss are retained in their cavities, the device is formed into a closed figure. The cleaning part of the toothpick can be released without disengagement of the dental floss. The dental floss can be released without disengagement of the cleaning part of the toothpick.

In another embodiment, a dental device for cleaning teeth comprising a length of dental floss, an elongated container with a cavity open in its first end and a connector. One end of the connector is attached to the second end of the container and the second end of the connector has a part adjusted for sealing the cavity of the container forming the device into a closed figure. The sealing part of the connector provides engagement with the first end of the container sealing its cavity. One end of the dental floss is affixed to the sealing part of the connector and the other end is affixed or not to the container inside its cavity and the dental floss is retained sanitary and releasably by the user of the device inside the cavity of the toothpick.

Any dental device when it is formed in a closed figure is adapted to be placed around another object, including a user's wrist, or a drinking cap, or utensils.

All drawings are magnified.

DETAILED DESCRIPTION OF THE PREFERRED EMBODIMENT

Figure 1:
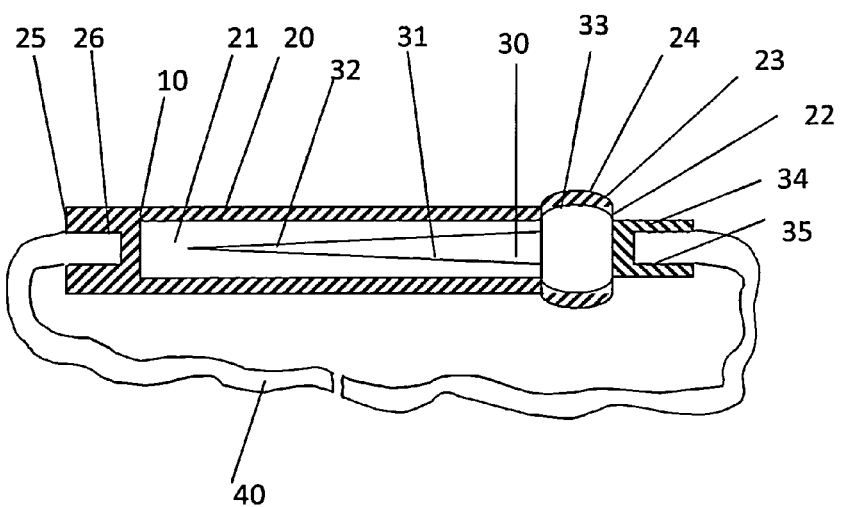
FIG. 1 shows a longitudinal cross section of the dental device 10.

FIG. 1 shows a longitudinal cross section of the dental device 10 including container 20, a toothpick 30, and a connector 40. Container 20 has a longitudinal cavity 21 with opening 22 at its end 23. The toothpick 30 with an elongated body has a first section defining as a pointed end 31 adapted for cleaning teeth. The cleaning part 31 with its end 32 is shown inserted into the cavity 21. The cavity 21 is adapted to receive at least the cleaning part 31 of the toothpick and retain it sanitary and releasably by the user of the device. bulging open end 24 of the container is adapted to snap a middle section defining as a bulge portion 33 of the toothpick and to provide sealing engagement between them. The protruding portion 25 of the container 20 is connected with a third section 34 of the toothpick 30 using the connector 40 which is made of bendable, flexible or elastic material wherein the third section 34 having a smaller diameter than the bulge portion 33. When the cleaning part 34 of the toothpick 30 is inserted into the container 20, the dental device 10 is formed into a closed figure. The end 25 of the container 20 has a hole 26 for connecting with one end of the connector 40. The end 34 of the toothpick has a hole 35 for connection with the other end of the connector 40.

Figure 2:
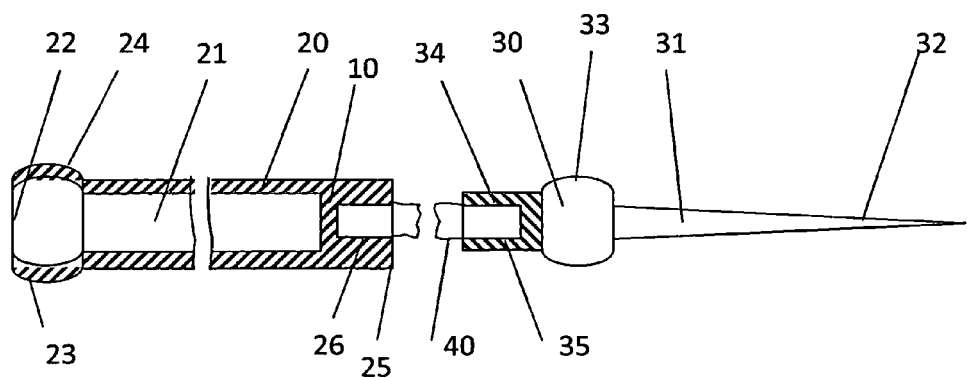
FIG. 2 depicts the dental device 10 with the released toothpick.

FIG. 2 shows the dental device 10 with the released toothpick 30. The lengths of the container 20, the part of the toothpick 30 insertable into the container 20 and the connector 40 are adjusted to allow insertion of at least the cleaning part 31 of the toothpick 30 into the cavity 21, removal the inserted part of the toothpick 30 from the cavity 21 by the user of the device and adjustment of the shape of the device 10 for its convenient use.

Figure 3:
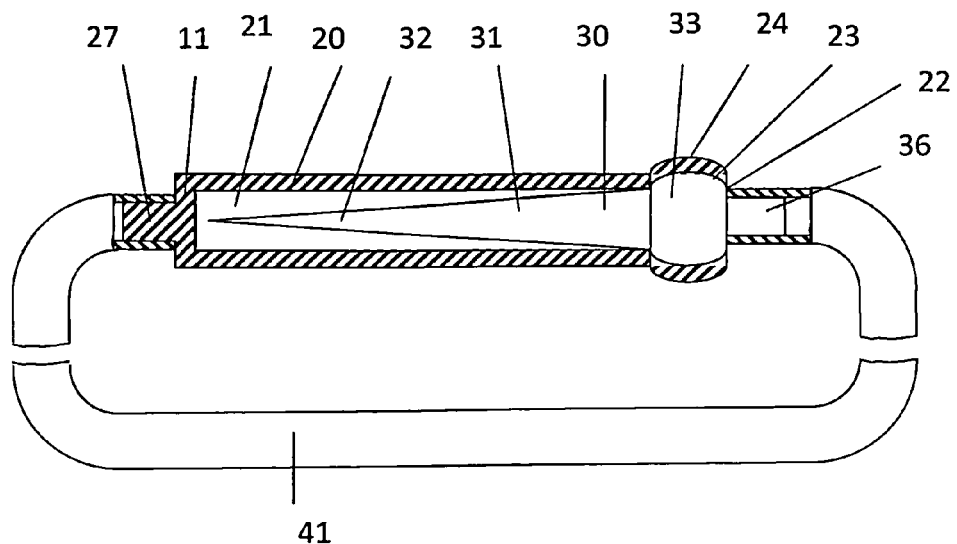
FIG. 3 shows a longitudinal cross section of a dental device 11.

FIG. 3 shows a longitudinal cross section of the dental device 11 including the container 20, the toothpick 30, and a connector 41. The container 20 has a longitudinal cavity 21 with opening 22 at its end 23. The toothpick 30 with an elongated body has a part 31 adapted for cleaning teeth. The cleaning part 31 with its end 32 is shown inserted into the cavity 21. The cavity 21 is adapted to receive the cleaning part 31 of the toothpick and retain it sanitary and releasably by the user of the device. The part 24 of the container is adapted to snap the part 33 of the toothpick and to provide sealing engagement between them. The end 27 of the container 20 is connected with the end 36 of the toothpick using connector 41 which is made of bendable, flexible or elastic material. When the toothpick 30 is inserted into the container 20, the dental device 11 is formed into a closed figure. The connector 41 is tubular.

Figure 4:
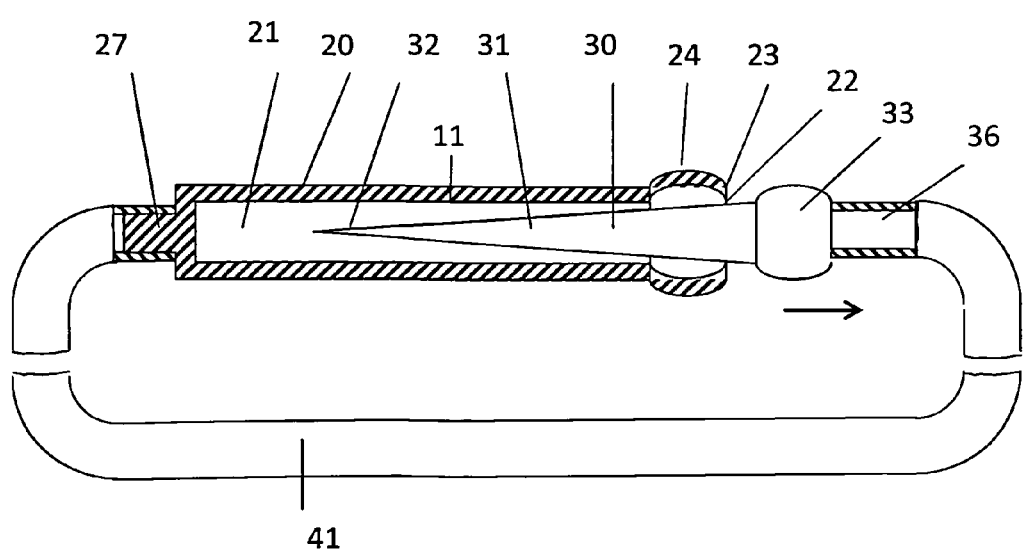
FIG. 4 shows the dental device 11 with the partially released toothpick.

FIG. 4 shows the dental device 11 with the partially released toothpick 30. The lengths of the container 20, the part of the toothpick 30 to be inserted into the container 20 and connector 41 are adjusted to allow insertion of at least the cleaning part 31 of the toothpick 30 into the cavity 21, removal the inserted part of the toothpick 30 from the cavity 21 by the user of the device and adjustment of the shape of the device 11 for its convenient use.

Figure 5:
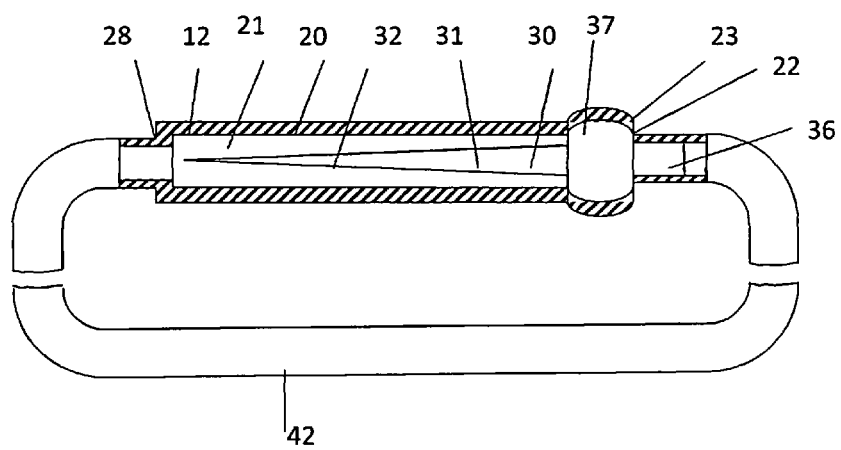
FIG. 5 shows a longitudinal cross section of a dental device 12.

FIG. 5 shows a longitudinal cross section of the dental device 12 including container 20, a toothpick 30, and a connector 42. The container 20 has a longitudinal cavity 21 with opening 22 at its end 23. The toothpick 30 with an elongated body has a part 31 adapted for cleaning teeth. The cleaning part 31 with its end 32 is shown inserted into the cavity 21. The cavity 21 is adapted to receive the cleaning part 31 of the toothpick and retain it sanitary and releasably by the user of the device. The diameter of the part 37 of the toothpick is bigger than the internal diameter of the cavity 21 at the end 23 of the container 20 in order to provide sealing engagement between them. The end 28 of the container 20 is connected with the end 36 of the toothpick using a connector 42 which is made of bendable, flexible or elastic material. When the toothpick 30 is inserted into the container 20, the dental device 12 is formed into a closed figure. The connector 42 and the container 20 are made as a single piece body. The connector 42 is tubular.

Figure 6:
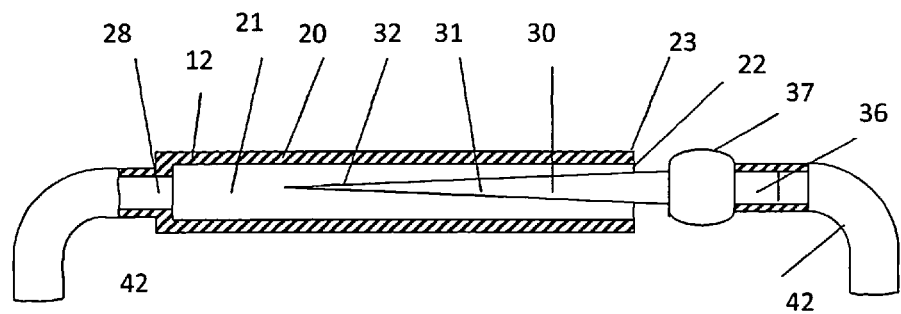
FIG. 6 shows the dental device 12 with the partially released toothpick.

FIG. 6 shows the dental device 12 with the partially released toothpick 30. The lengths of the container 20, the part of the toothpick 20 to be inserted into the container 20 and connector 42 are adjusted to allow insertion of at least the cleaning part 31 of the toothpick 30 into the cavity 21, removal the inserted part of the toothpick 36 from the cavity 21 by the user of the device and adjustment of the shape of the device 12 for its convenient use.

Figure 7:
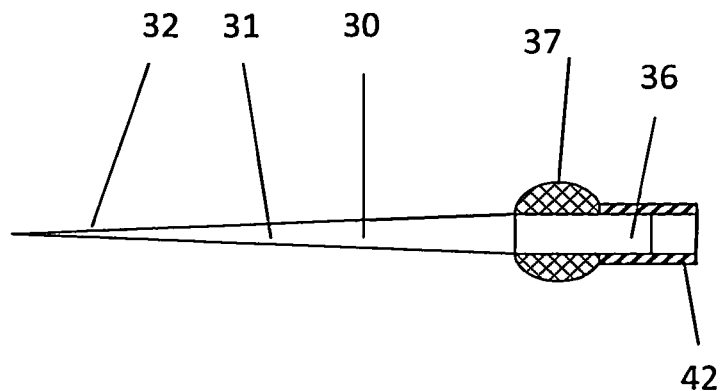
FIG. 7 shows a toothpick with its end attached to the connector.

FIG. 7 shows the toothpick 30 with its end 36 attached to the connector 42. The diameter of the part 37 is bigger than the internal diameter of the cavity 21 of the container 20 in order to provide sealing engagement between them. The part 37 is made of elastic material.

Figure 8:
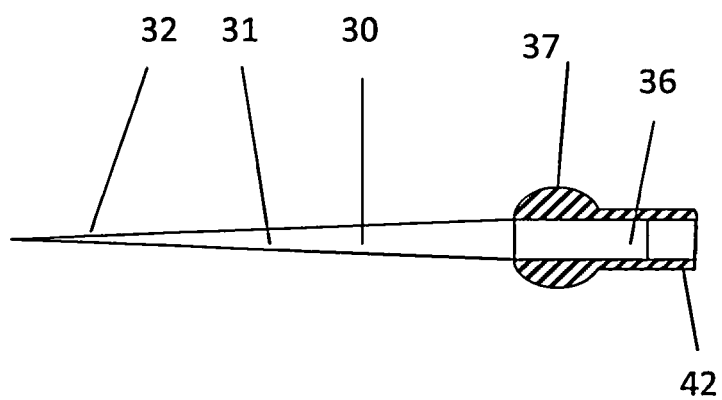
FIG. 8 shows a toothpick attached to the connector.

FIG. 8 shows the toothpick 30 with its end 36 attached to the connector 42. The diameter of the part 37 is bigger than internal diameter of the cavity 21 of the container 20 in order to provide sealing engagement between them. The part 37 and connector 42 are made as a single piece body. It can be made of elastic material.

Figure 9:
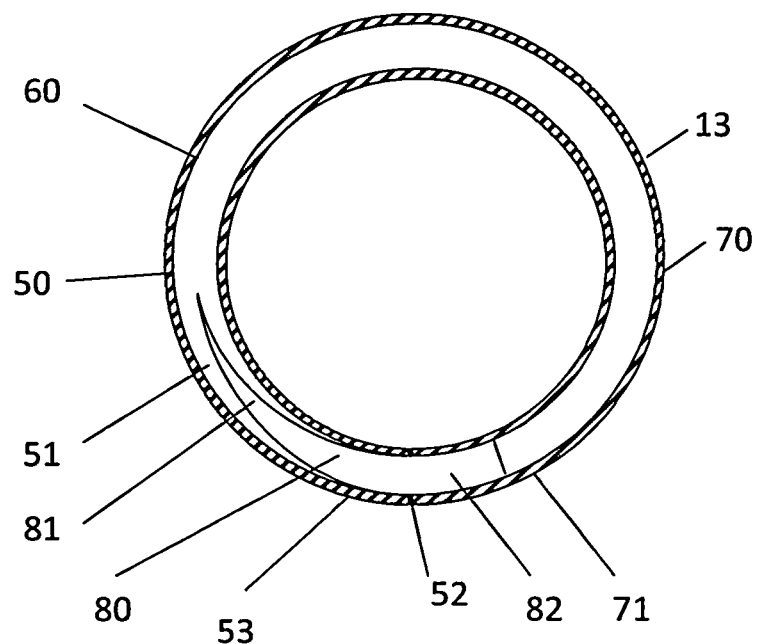
FIG. 9 shows a cross section of the dental device 13.

FIG. 9 shows a cross section of the dental device 13 including a container 50 and a connector 60 made as a tubular single piece body 70 with an internal hole 51, a with opening 52 at its end 53. The toothpick 80 with an elongated body has a part 81 adapted for cleaning teeth. The cleaning part 81 is shown inserted into the cavity 51. The cavity 51 is adapted to receive the cleaning part 81 of the toothpick and retain it sanitary and releasably by the user of the device.

Between the cavity 51 of the container 50 and toothpick 80 is provided sealing engagement. The end 71 of the body 70 is connected with the end 82 of the toothpick 80. When the cleaning part 81 of the toothpick 80 is inserted into the container 50, the figure formed by the dental device 13 is a circle. The body 70 is tubular. It can be made of bendable, flexible or elastic material.

Figure 10:
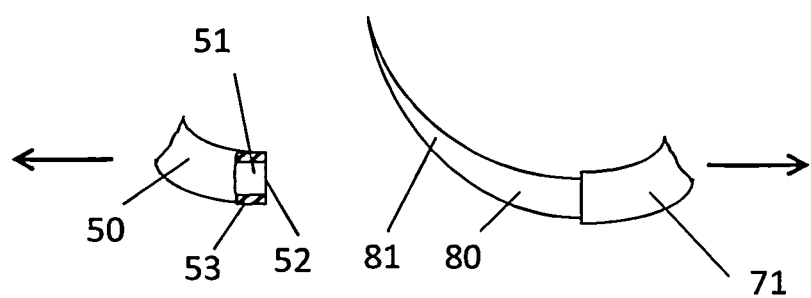
FIG. 10 shows the toothpick 80 slightly released from the container 50.

FIG. 10 shows the toothpick 80 slightly released from the container 50. The cleaning part 81 of the toothpick 80 has a curved shape needed for retaining it in the curved container 50. The cleaning part 81 of the toothpick 80 retains its curved shape after removing it from the curved container 50. A curved toothpick is more convenient for cleaning teeth than a straight toothpick.

Figure 11:
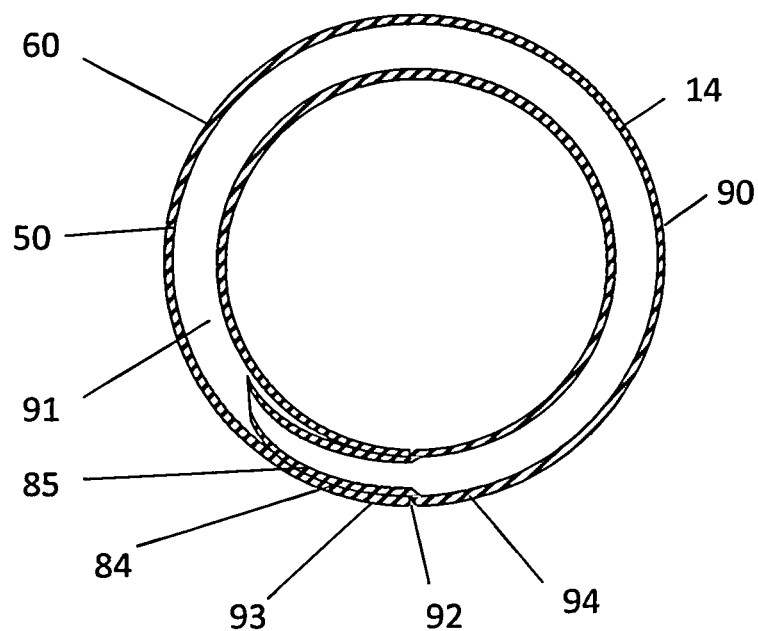
FIG. 11 shows a cross section of a dental device 14.

FIG. 11 shows a cross section of the dental device 14. The container 50, the connector 60 and the toothpick 84 are made as a tubular single piece body 90. The body 90 has an internal cavity 91, with an opening 92 at its end 93. The toothpick 84 with an elongated body has a part 85 adapted for cleaning teeth. The cleaning part 85 is inserted into the cavity 91. The cavity 91 is adapted to receive the cleaning part 85 and retain it sanitary and releasably by the user of the device. Between the end 93 of the cavity 91 and the toothpick 84 is provided sealing engagement. When the cleaning part 85 of the toothpick 84 is inserted into the cavity 91, the figure formed by the dental device 14 is a circle. The body 90 can be made bendable, flexible or elastic.

Figure 12:
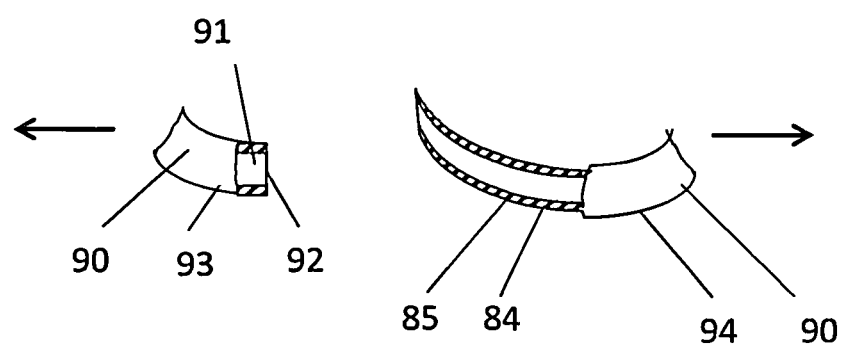
FIG. 12 shows the toothpick 84 slightly released from the cavity 91.
Figure 13:
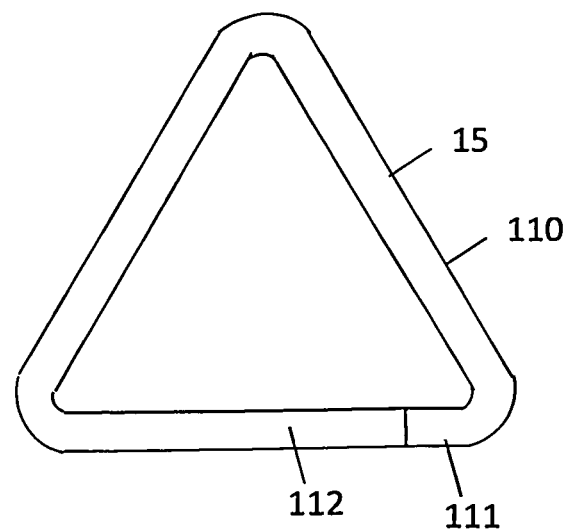
FIG. 13-FIG. 16 show the dental device 15 as a triangle and its cross sections.

FIG. 12 shows the toothpick 84 slightly released from the cavity 91. The cleaning part 85 of the toothpick 84 has a curved shape needed for retaining it in the curved cavity 91. The cleaning part 85 of the toothpick 84 retains its curved shape after removing it from the cavity 91.

Figure 14:
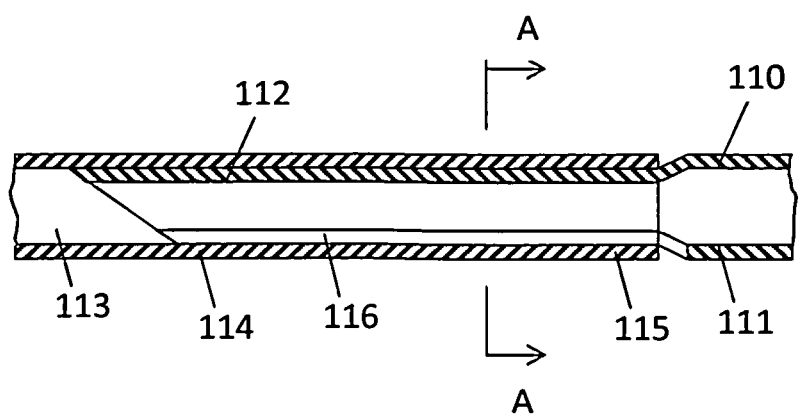
Figure 15:
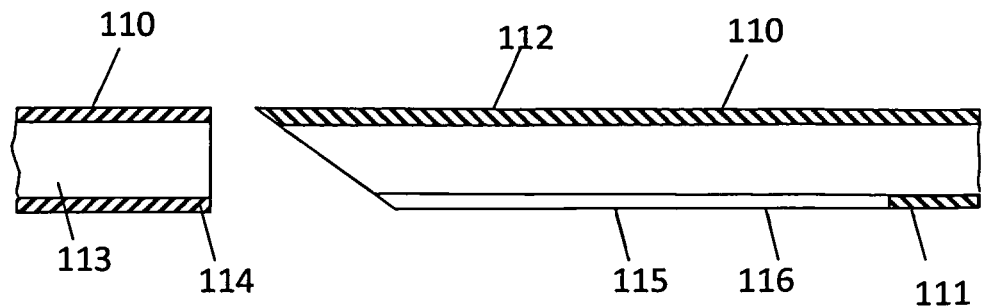
Figure 16:
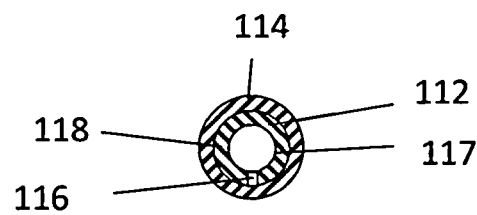

FIG. 13-FIG. 16 show the dental device 15 formed as a triangle and cross sections of its cleaning part 112 inserted into the cavity 113 of the container part 114. The device is made as a tubular single piece body 110. When its end 111 with the cleaning part 112 is inserted into the cavity 113 in its other end 115, the device is formed as a triangle. FIG. 14 shows cross section of the cleaning part 112 inserted into the container part 114. The cleaning part 112 has a longitudinal slot 116. The slot 116 splits the cleaning part into two halves 117 and 118 allowing them to flex relative to each other. The diameter of the cleaning part 112 is the same as diameter of the end 115. Due to flexibility of halves 117 and 118 the cleaning part 112 can be inserted into the of the cavity 113 providing sealing engagement between them. FIG. 15 shows the cleaning part 112 before its insertion into the container part 114. FIG. 16 shows cross section made along A-A.

Figure 17:
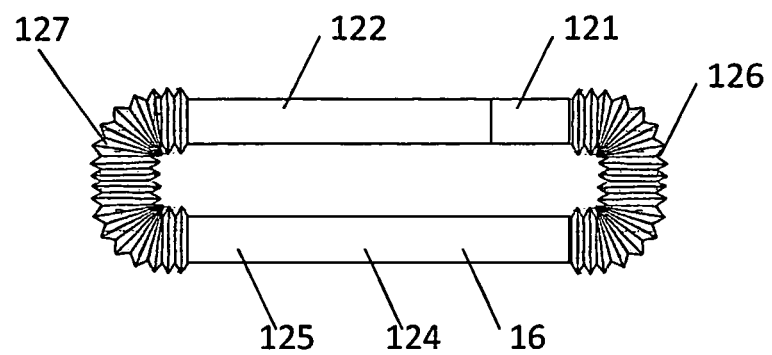
FIG. 17 shows the dental device 16.

FIG. 17 shows the dental device 16 with its end 121 having a cleaning part (not shown) is inserted into the container 122. The device is made as a single tubular body 124. A connector 125 has two bendable parts 126 and 127 made as bellows like bellows used in flexible straws. The sealing engagement between the cleaning part and the container 122 can be provided in the same way as in the dental device 15 shown in the FIG. 14-16.

Figure 18:
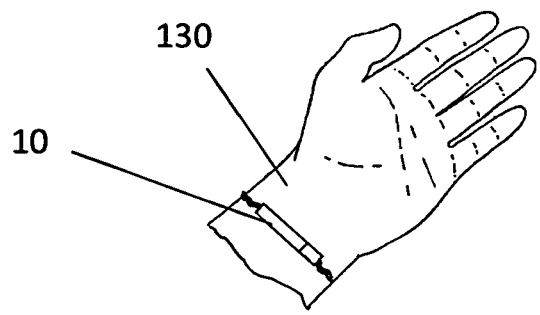
FIG. 18 shows a dental device placed around a user's wrist.

FIG. 18 shows a dental device, for example, the dental device 10 placed around a user's wrist 130. The device can be placed around a user's wrist with or without releasing the cleaning part of the toothpick. The dental device can be worn as a wrist band. In order to use the device, the user has to remove the dental device from wrist 130 using elasticity of the connector or by disengagement of the cleaning part of the device from its container.

Figure 19:
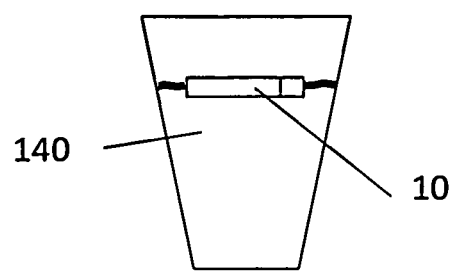
FIG. 19 shows a dental device placed around a drinking cup.

FIG. 19 shows a dental device, for example, the dental device 10 placed around a drinking cup 140. The device can be placed around the cup with or without releasing the cleaning part of the toothpick. The device can be held in place due to, for example, elasticity of the connector. In order to use the device, the user has to remove the dental device from the cup 140 using elasticity of the connector or by disengagement of the cleaning part of the device from its container.

Figure 20:
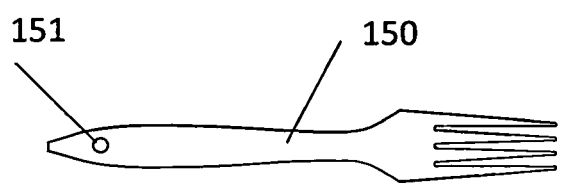
FIG. 20 shows a fork with a hole.

FIG. 20 shows a fork 150 with a hole 151.

Figure 21:
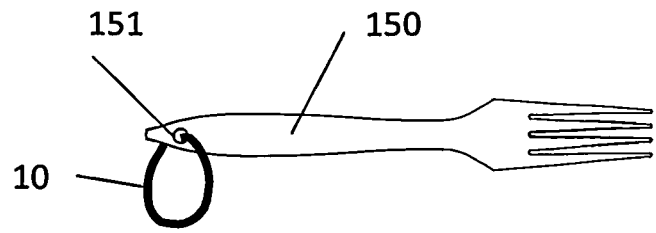
FIG. 21 shows a dental device placed through the hole in the fork.

FIG. 21 shows a dental device 10 placed through the hole 151 in the fork 150. A method of attachment of the dental device, for example, dental device 10 to an object, for example, utensil, includes the steps of providing the object with a hole 150, inserting one end of the dental device 10 through the hole 150 and inserting the cleaning member into the container forming the device into a closed figure and providing sealing engagement between the container and the toothpick. In order to use the device, the user has to disengage the cleaning part of the device from its container and remove the dental device from the fork 150.

Figure 22:
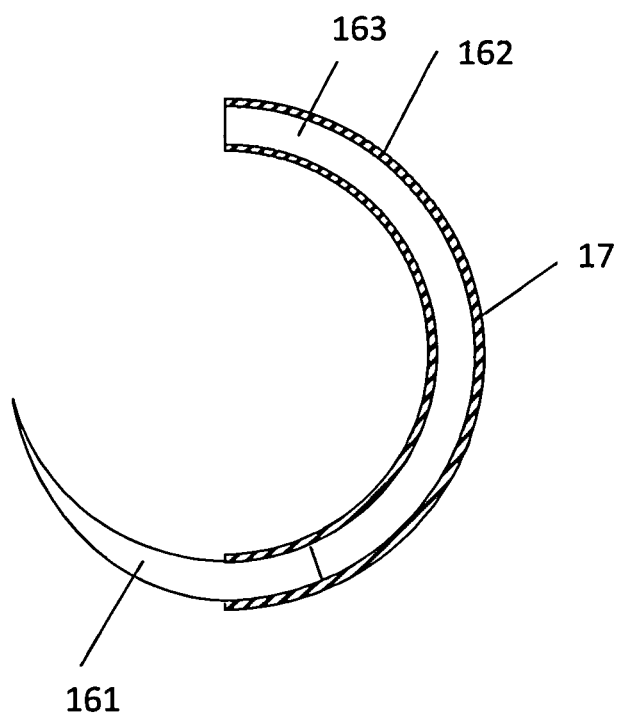
FIG. 22 shows a cross section of the dental device 17.

FIG. 22 shows a cross section of the dental device 17 which is similar to the dental device 13. Its cleaning part 161 is connected with a single piece body 162 with a cavity 163 adjusted for receiving a cleaning part and retain it sanitary and releasably by the user of the device. The cleaning part 161 is curved to match a curvature of the container.

Figure 23:
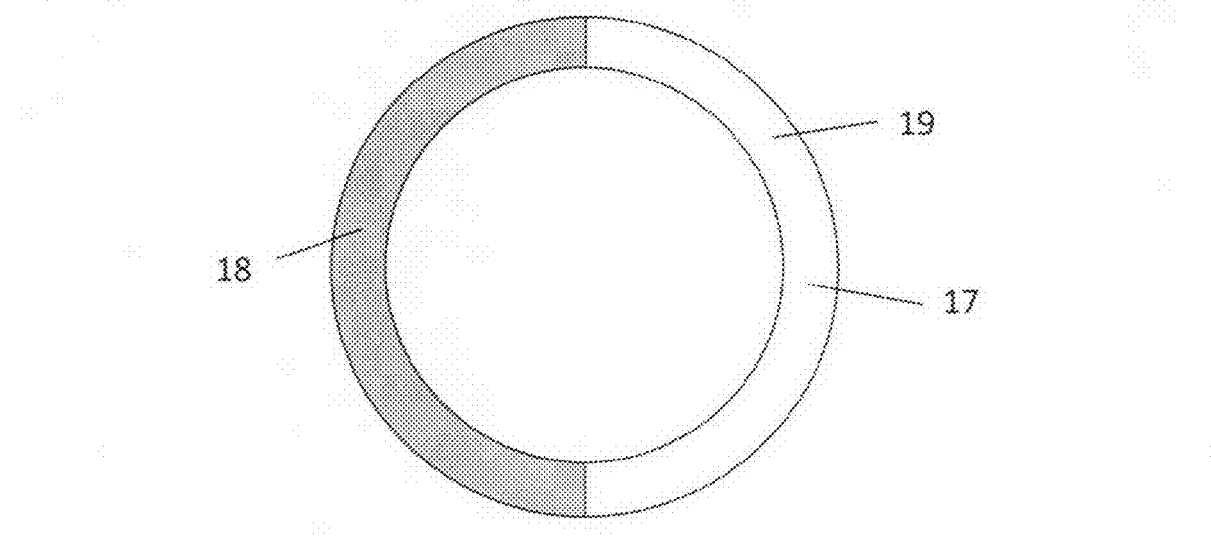
FIG. 23 shows the dental device 19.

FIG. 23 shows a dental device 19 comprising dental device 17 and a similar dental device 18. The dental device 18 has a different color.

Figure 24:
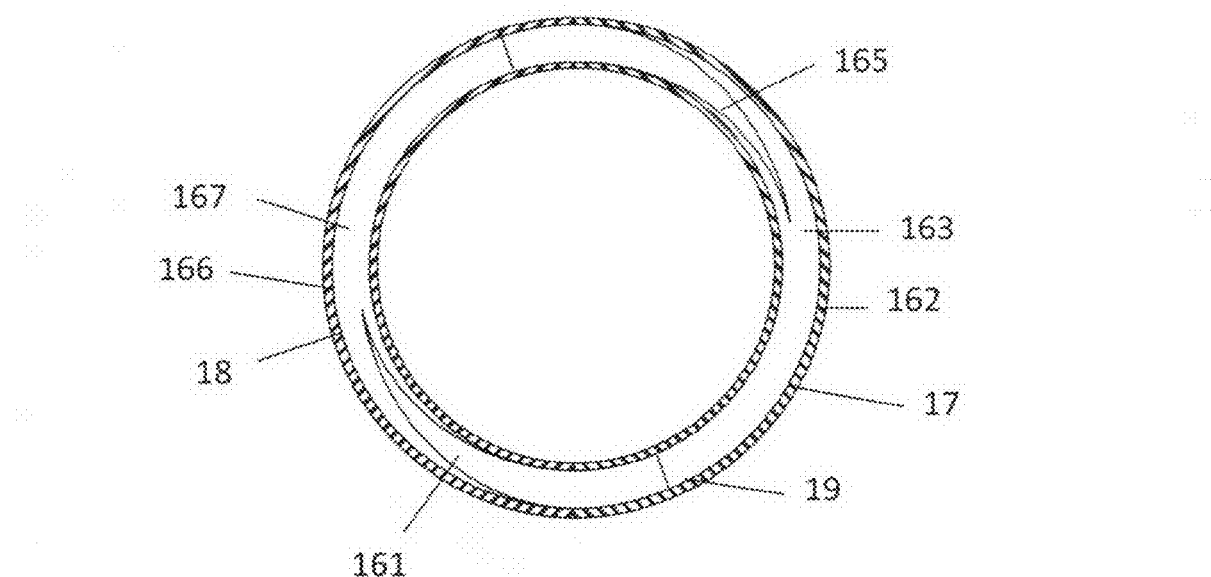
FIG. 24 shows a cross section of the dental device 19.

FIG. 24 shows a cross section of the dental device 19. The cleaning part 165 of the dental device 18 is connected with a single piece body 166 with a cavity 167 adjusted for receiving a cleaning part and retain it sanitary and releasably by the user of the device. The cleaning part 161 of the dental device 17 is inserted into the cavity 167 of the dental device 18 and retained sanitary and releasably by the user of the device. The cleaning part 165 of the dental device 18 is inserted into the cavity 163 of the dental device 17 and retained sanitary and releasably by the user of the device. The dental device 19 is formed into a closed figure. The cleaning part 161 of the dental device 17 can be released by the user of the device with or without disengagement the device 17 from the device 18. The cleaning part 165 of the dental device 18 can be released by the user of the device with or without disengagement the device 18 from the device 17.

Figure 25:
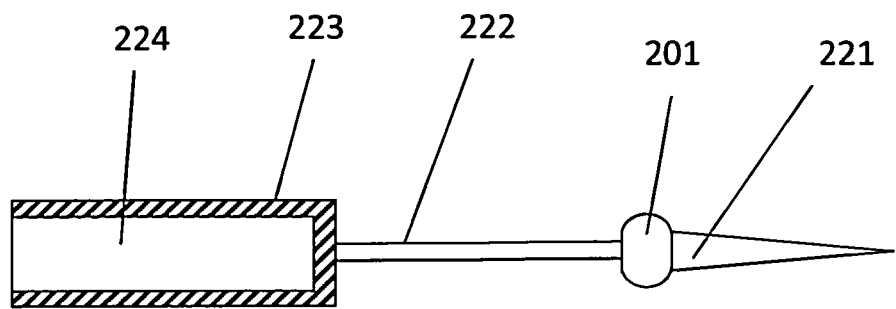
FIG. 25 shows the dental device 201.

FIG. 25 shows the dental device 201 which is similar to the dental devices 10-12. The cleaning part 221 is connected with the connector 222. The connector 222 is connected with the container 223 having the cavity 224 adjusted for receiving a cleaning part and retain it sanitary and releasably by the user of the device.

Figure 26:
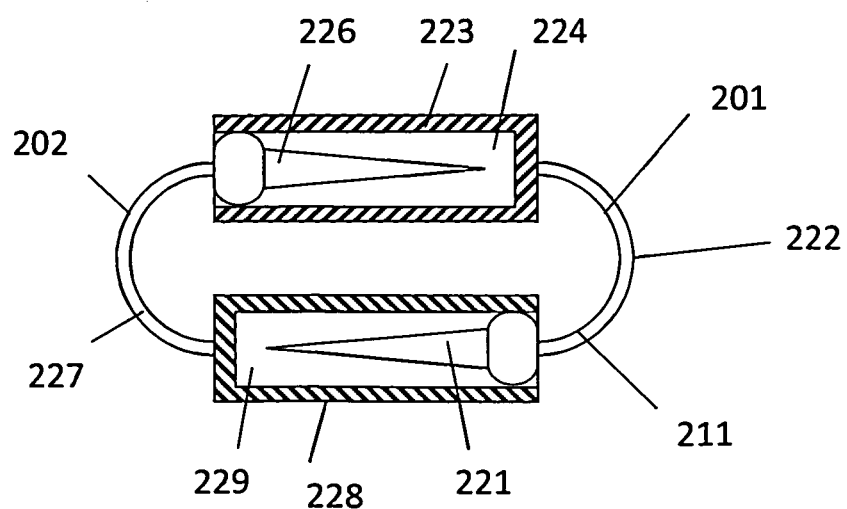
FIG. 26 shows the dental device 211.

FIG. 26 shows a dental device 211 having two similar dental devices 201 and 202. The cleaning part 226 of the device 202 is connected with a connector 227. The connector 227 is connected with the container 228 having the cavity 229 adjusted for receiving a cleaning part and retain it sanitary and releasably by the user of the device. The cleaning part 221 of the dental device 201 is inserted into the cavity 229 of the dental device 202 and retained sanitary and releasably by the user of the device. The cleaning part 226 of the dental device 202 is inserted into the cavity 224 of the dental device 201 and retained sanitary and releasably by the user of the device. The dental device 211 is formed into a closed figure. The cleaning part 221 can be released by the user of the device with or without disengagement the device 201 from the device 202. The cleaning part 226 can be released by the user of the device with or without disengagement the device 202 from the device 201. The devices 201 and 201 can be disengaged from each other. The device 201 can be formed into a closed figure by inserting its cleaning part 221 into its own cavity 224. The device 202 can be formed into a closed figure by inserting its cleaning part 226 into its own cavity 229. The devices o at least their containers and/or connectors can have different colors.

Figure 27:
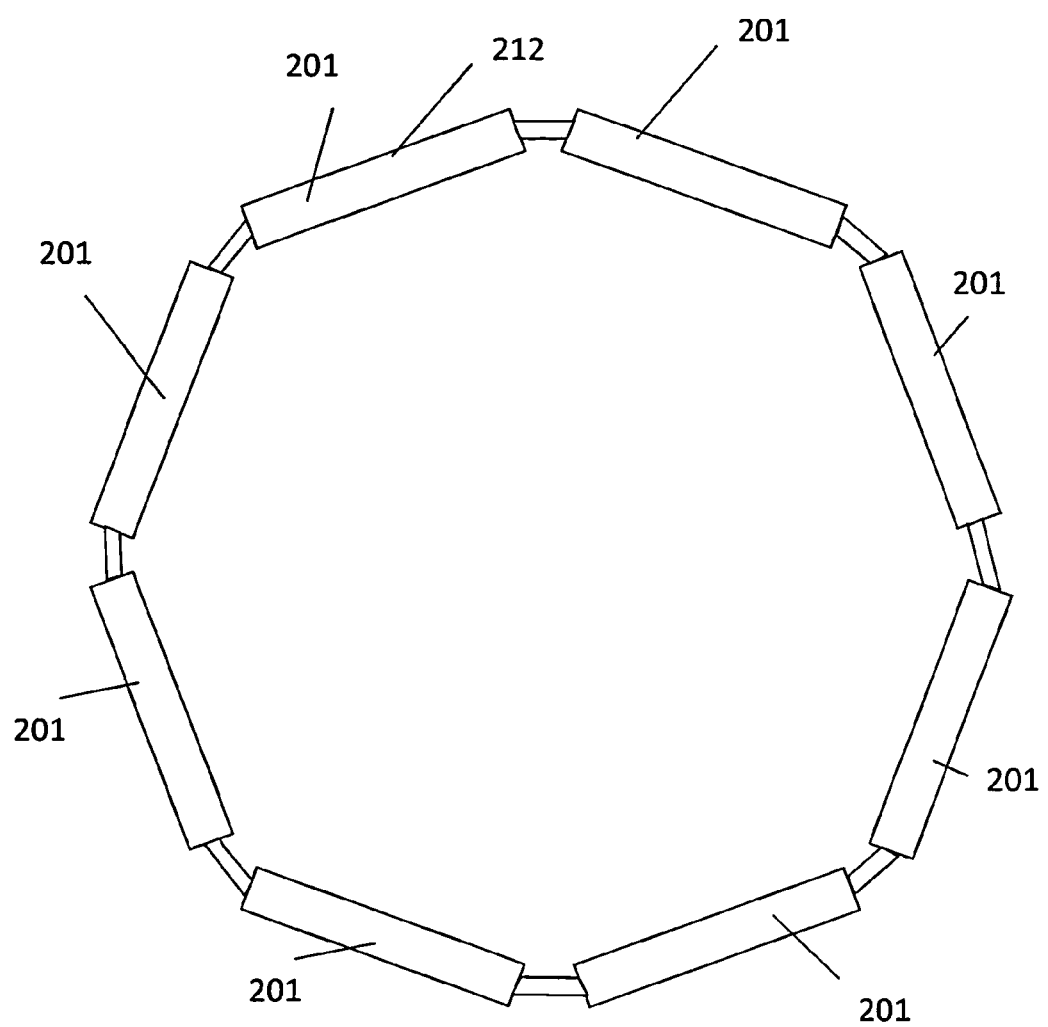
FIG. 27 shows the dental device 212.

FIG. 27 shows the dental device 212 which is similar to the device 211. The device 212 comprises 8 devices like device 201. All devices 201 are positioned and aligned in such a way so the cleaning part of each device is inserted into the cavity of the container of the adjusting device forming a closed figure and each cavity retains the inserted cleaning member sanitary and releasably by the user of the device. After removing one device 201 for use, the adjacent devices are engaged to form a new closed figure. For example, after removing the first device 201, a new closed figure will have 7 devices 201, etc. All devices can be formed into individual closed figures. As an alternative, at least one of the devices intended to be last one used by the user can be formed into a closed figure. The devices can have different colors.

Figure 28:
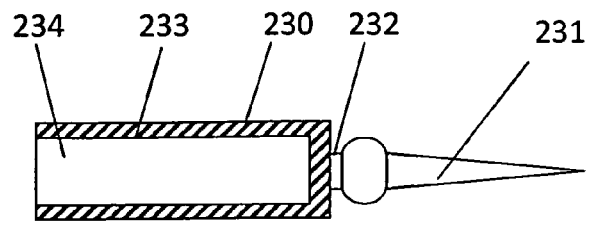
FIG. 28 shows the dental device 230.

FIG. 28 shows a dental device 230 which is similar to the dental devices 10-12. The cleaning part 231 is connected with connector 232 which is connected with the container 233 having the cavity 234 adjusted for receiving a cleaning part and retain it sanitary and releasably by the user of the device. The connector 232 can be short or even absent.

Figure 29:
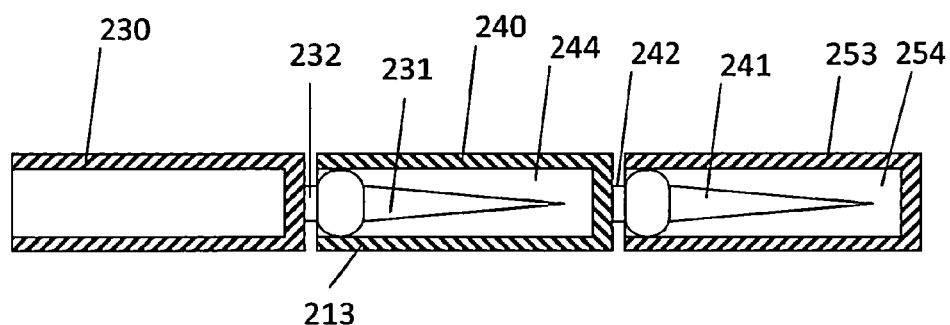
FIG. 29 shows the dental device 213.

FIG. 29 shows the dental device 213 comprising the dental device 230 and a similar dental device 240. The cleaning part 241 is connected with the connector 242. The connector 242 can be short or even absent. The connector 242 is connected with the container 243 having the cavity 244 adjusted for receiving a cleaning part and retain it sanitary and releasably by the user of the device. The device 212 can include 2-10 or more dental devices similar to device 230. The cleaning part 231 of the dental device 230 is inserted into the cavity 244 of the dental device 240 and retained sanitary and releasably by the user of the device. The cleaning part 241 of the dental device 240 is inserted into the cavity 254 of container 253 and retained sanitary and releasably by the user of the device.

Figure 30:
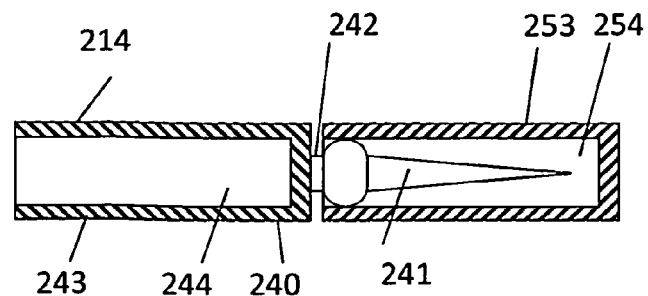
FIG. 30 shows the dental device 214.

FIG. 30 shows the dental device 214 which is obtained from the dental device 213 after disengagement of the device 230 for its use.

Figure 31:
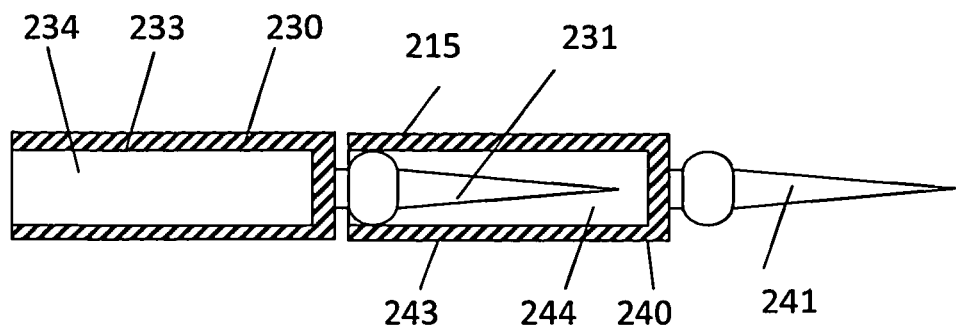
FIG. 31 shows the dental device 215.

FIG. 31 shows the dental device 215 which is obtained from the device 213 after removal of the container 250.

Figure 32:
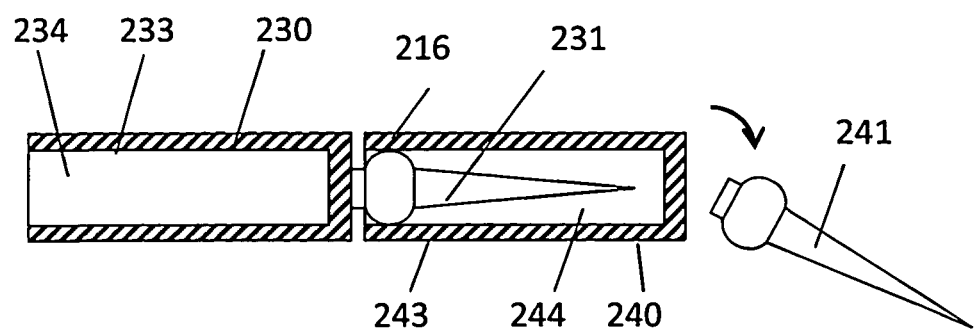
FIG. 32 shows the dental device 216.

FIG. 32 shows a dental device 216 which is obtain from the device 215 after breaking away the used cleaning part 241. The cleaning parts of the devices 230 or 240 or their connectors 232 and 242 are adapted to be broken away by the user after their use by providing them with a break point.

Figure 33:
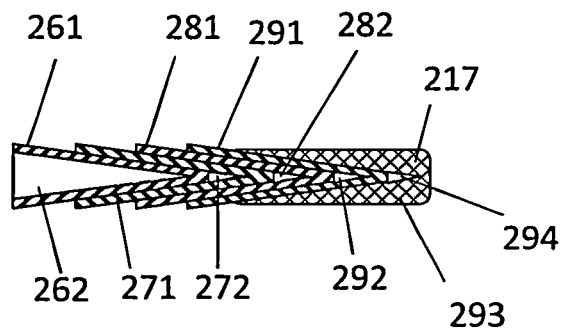
FIG. 33 shows the dental device 217.

FIG. 33 shows the dental device 217 comprising similar or identical dental devices 261, 271, 281 and 291. Their cavities 262, 272, 282 and 292 are adjusted for receiving a cleaning part of the adjusting device and retain it sanitary and releasably by the user of the device. The device 217 can include 2-10 or more dental devices similar or identical to the device 261. The cavity of each dental device is extended into the cleaning part of its device. For example, the cavity 272 of the device 271 is extended into the cleaning part of the device 271 and is adjusted to for insertion and holding in this area a part of the cleaning part of the dental device 261. The cleaning part of the last dental device 291 is into the cavity 293 of the container 293 and retained sanitary and releasably by the user of the device. The user of the device 217 removes the device 261 first and discards it after use. When it is needed, the user removes the device 271, etc. The devices 261, 271, 281 and 291 can have different colors.

Figure 34:
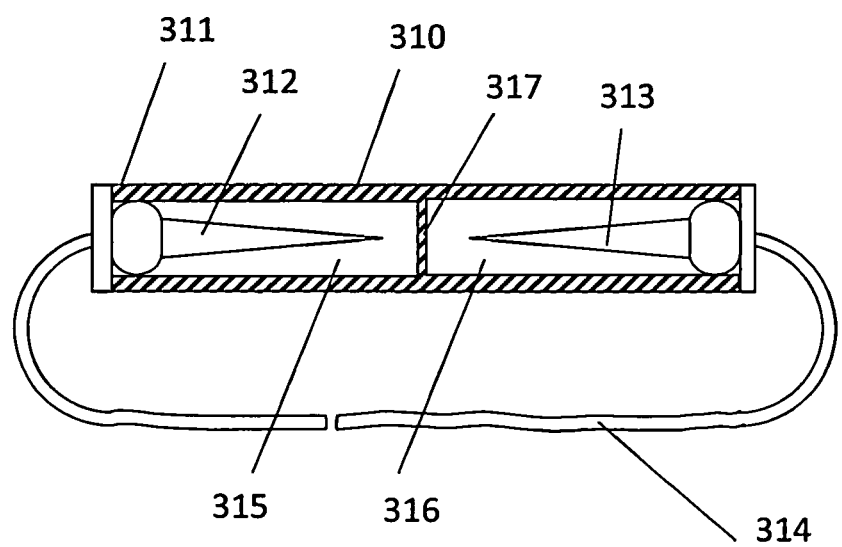
FIG. 34 shows a longitudinal cross section of the dental device 310.

FIG. 34 shows a longitudinal cross section of the dental device 310 including a tubular container 311, toothpicks 312 and 313, and a connector 314. The container 311 has a longitudinal cavity open at both ends. The cavity can be separated into two sanitary sections 315 and 316 by the barrier 317 which can be a part of the container or not. At least the cleaning of the toothpick 312 is inserted into the cavity 315. At least the cleaning of the toothpick 313 is inserted into the cavity 316. The cavities 315 and 316 are adapted to receive at least cleaning part of the toothpicks 312 and 313 and retain them sanitary and releasably by the user of the device. The other ends of the toothpicks are connected by the connector 314. When the toothpicks 312 and 313 are inserted into the container 314, the dental device 310 is formed into a closed figure.

Figure 35:
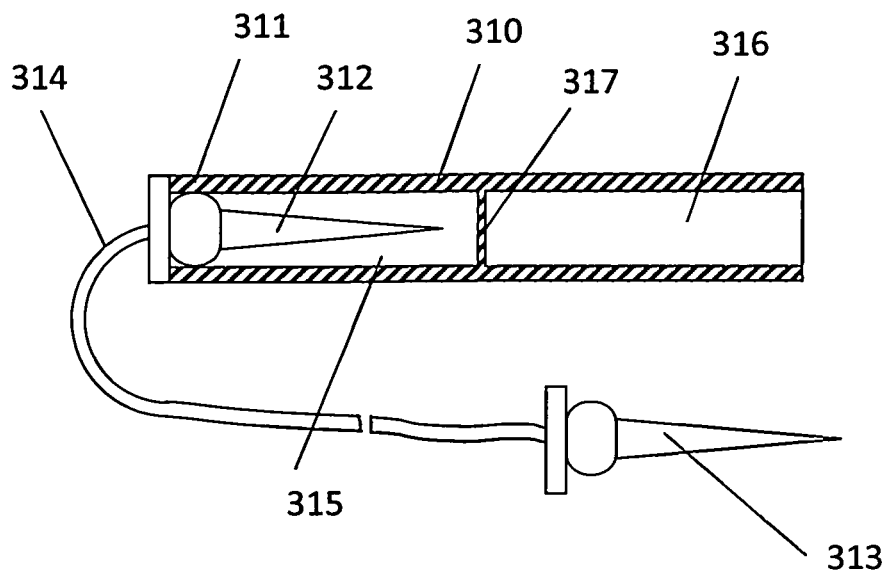
FIG. 35 shows the dental device 310 with a released toothpick.

FIG. 35 shows the dental device 310 with released toothpick 313.

Figure 36:
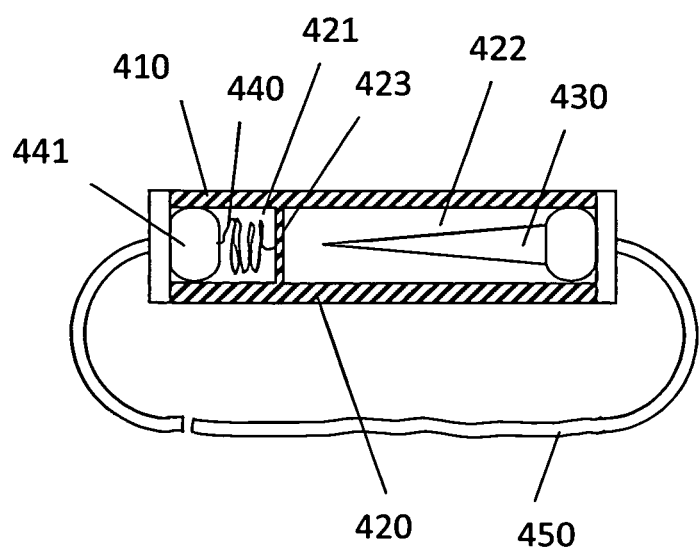
FIG. 36 shows a longitudinal cross section of the dental device 410.

FIG. 36 shows a longitudinal cross section of the dental device 410 including a container 420, a toothpick 430, a length of dental floss 440 and a connector 450. The container 420 has a longitudinal cavity open at both ends. The cavity can be separated into two sanitary sections 421 and 422 by the barrier 423 which can be a part of the container 420 or not. At least the cleaning part of the toothpick 430 is inserted into the cavity 422 which is adapted to receive at least cleaning part of the toothpicks 430 and retain it sanitary and releasably by the user of the device. The other end of the toothpick 430 is connected with a connector 450. The length of dental floss 440 is retained sanitary and releasably by the user of the device in the cavity 421. One end of the floss 440 is affixed to the one side of the part 441 used to seal the floss 440 in the cavity 421 and pull it out of the cavity when the floss 440 is needed. The other end of the floss can be affixed to the container or barrier 423 inside the cavity 421. The other side of the part 441 is connected to the connector 450. The connector 450 and the part 441, the connector 450 and the toothpick 430 or the connector 450, the part 441 and the toothpick 430 can be made as a single piece body. When both the toothpick 430 and the floss 440 are retained in their respective cavities, the dental device 410 is formed into a closed figure.

Figure 37:
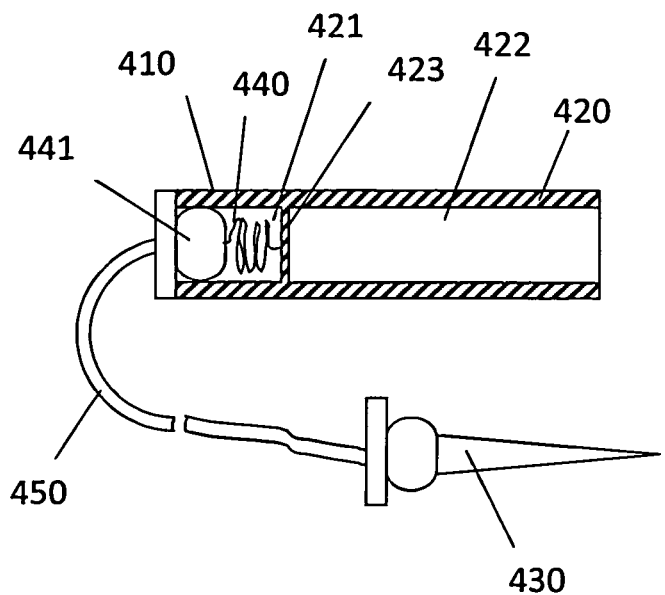
FIG. 37 shows the dental device 410 with the released toothpick 430.

FIG. 37 shows the dental device 410 with the released toothpick 430. The user can adjust the shape of the connector 450 for convenient use of the toothpick 430. Releasing the toothpick 430 does not affect retaining of the floss 440 in the cavity 421.

Figure 38:
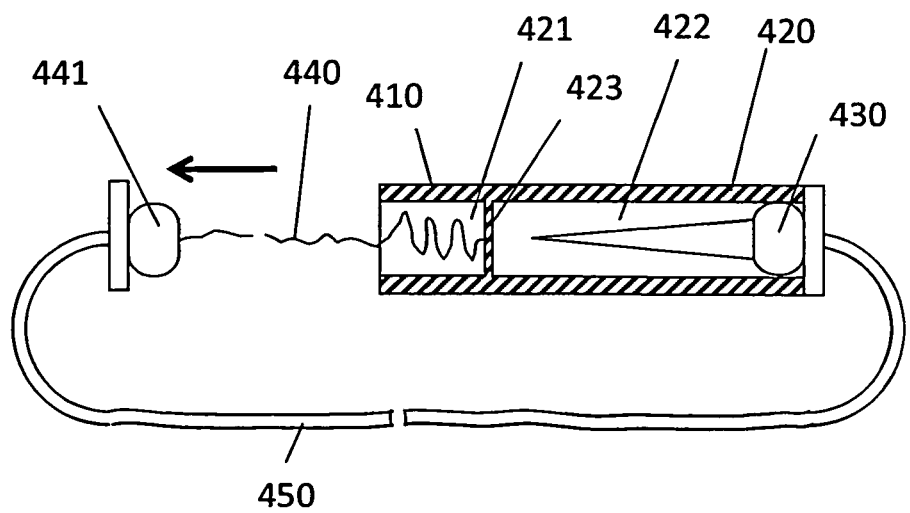
FIG. 38 shows the dental device 410 with the released dental floss 440.

FIG. 38 shows the dental device 410 with the released dental floss 440. The arrow shows the direction of pulling the part 441. Releasing the dental floss 440 from the cavity 421 does not affect retaining of the toothpick 430 in the cavity 422.

Figure 39:
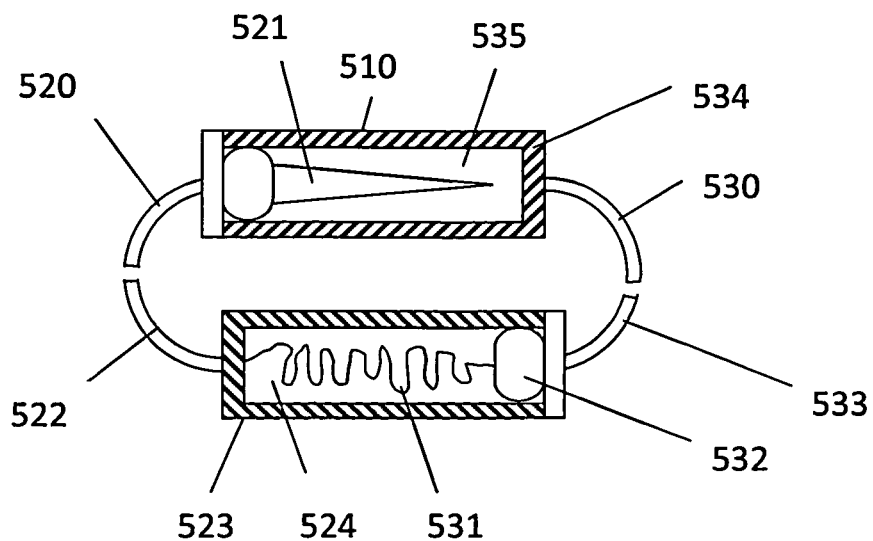
FIG. 39 shows a longitudinal cross section of the dental device 510.

FIG. 39 shows a longitudinal cross section of the dental device 510 comprising two dental cleaning devices 520 and 530. The dental cleaning device 520 has the toothpick 521 connected with the connector 522 which connected with the container 523. The dental cleaning device 530 has the length of dental floss 531 attached to the part 532. The part 532 is connected with the connector 533 which is connected with the container 534. The cleaning part of the toothpick 521 is inserted into the cavity 535 of the container 534 where it is retained sanitary and releasably by the user of the device. The other end of the toothpick 521 is connected with a connector 522. The length of dental floss 531 is retained sanitary and releasably by the user of the device in the cavity 524 of the container 523. One end of the floss 531 is affixed to one side of the part 532 adjusted to seal the floss in the cavity 524 and pull it out of the cavity when the floss needed. The other end of the floss can be either affixed to the container 523 inside the cavity 524 or not attached. The other side of the part 532 is connected to the connector 533. The connector 533 and the part 532, or the connector 533, the part 532 and the container 534 can be made as a single piece body. The connector 522 and the container 523 or the container 522, the container 523 and the toothpick 521 can be made as a single piece body. When both the toothpick 521 and the dental floss 531 are retained in their respective cavities, the dental device 510 is formed into a closed figure. The toothpick 521 can be released and used by the user of the device regardless of the engagement or disengagement of the part 532. The dental floss 531 can be released and used by the user of the device regardless of the engagement or disengagement the toothpick 521. The containers 523 and 534 can be identical. The containers can have different colors to distinguish the toothpick from dental floss.

Figure 40:
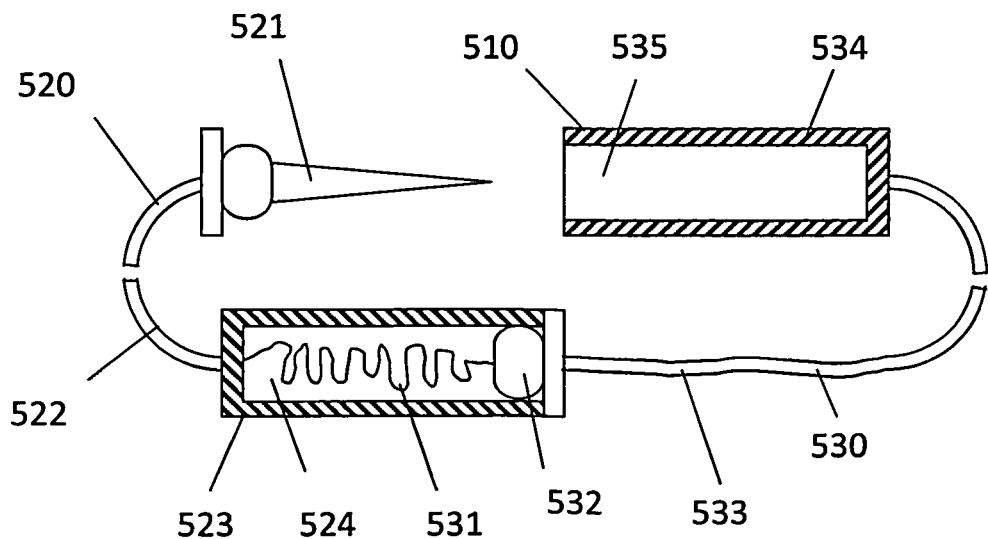
FIG. 40 shows the dental device 510 with the slightly released toothpick 521.

FIG. 40 shows the dental device 510 with the slightly released toothpick 521. The user can adjust the shape of the connector 520 for convenient use of the toothpick 521. Releasing the toothpick 430 does not affect retaining of the floss 531 in the cavity 524.

Figure 41:
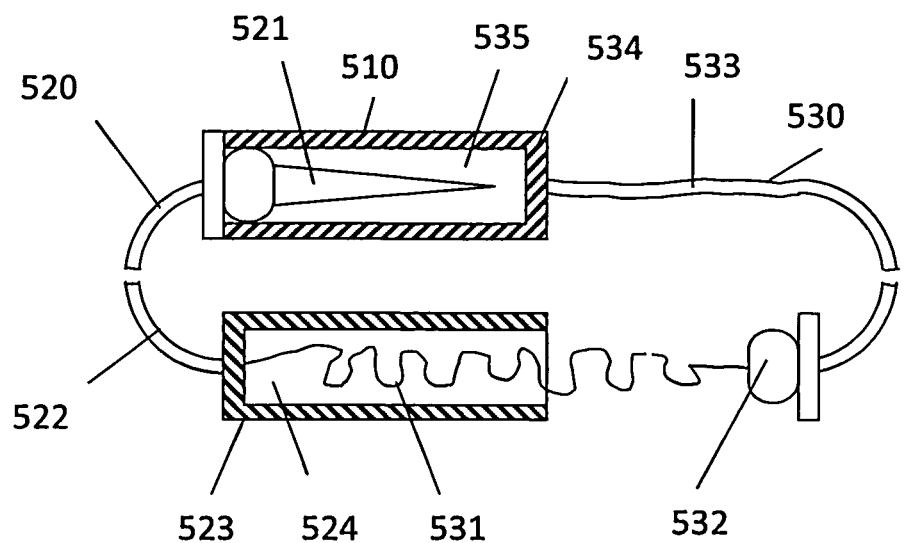
FIG. 41 shows the dental device 510 with the slightly released dental floss 531.

FIG. 41 shows the dental device 510 with the slightly released dental floss 531. The Releasing the dental floss 531 from the cavity 524 does not affect retaining of the toothpick 521 in the cavity 535.

Figure 42:
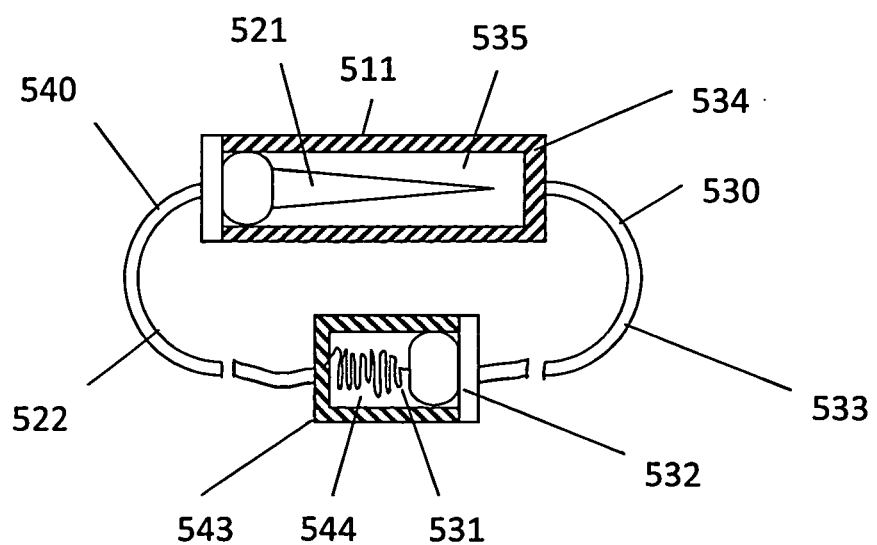
FIG. 42 shows the dental device 511.

FIG. 42 shows the dental device 511 which is similar to the dental device 510. The only difference is the container 543 of the dental device 540 is shorter than the container 523 of the device 520. Container for retaining the dental floss 531 can be made smaller and/or have different color.

Figure 43:
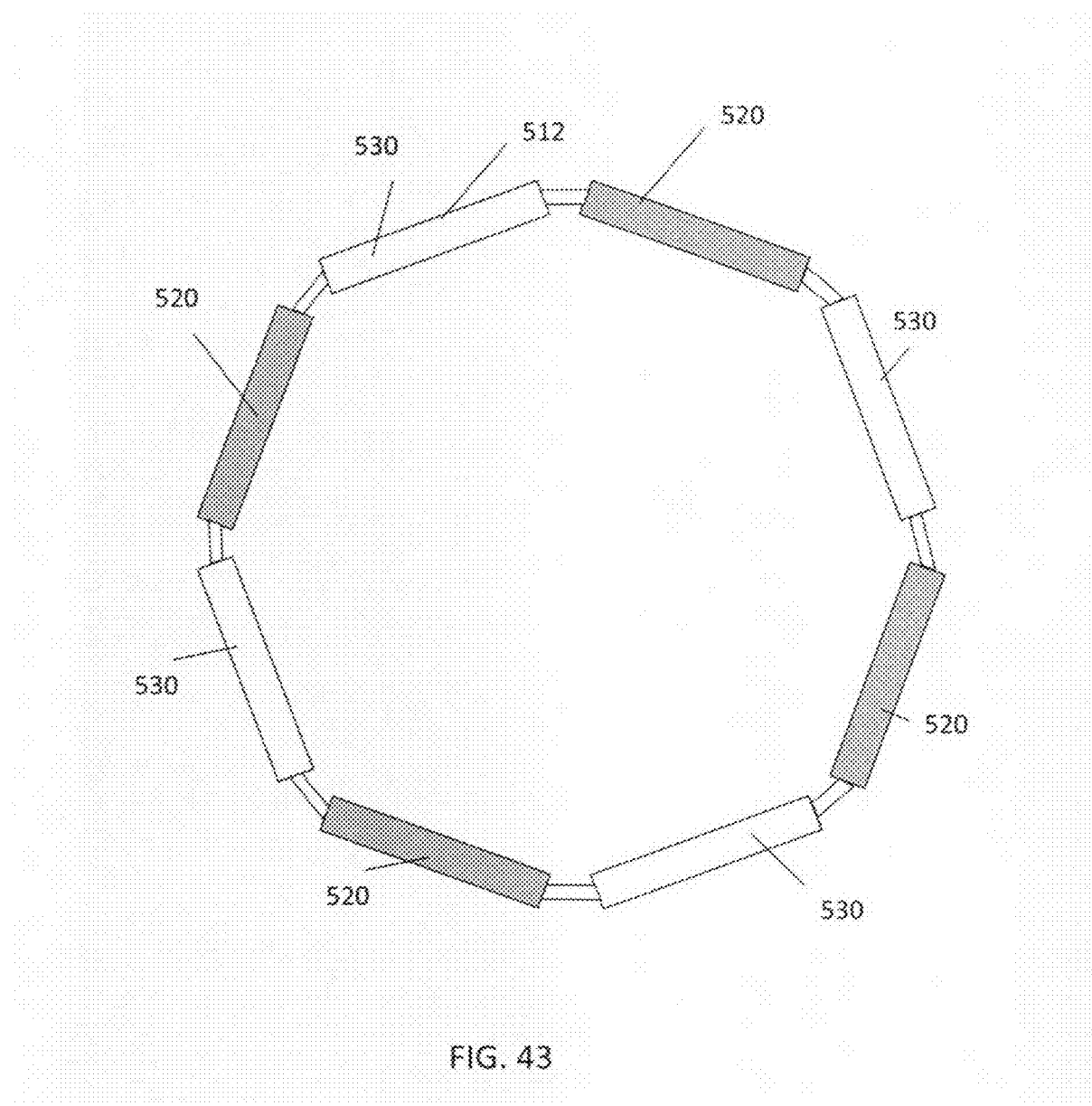
FIG. 43 and FIG. 44 show front and side views of the dental device 512.
Figure 44:
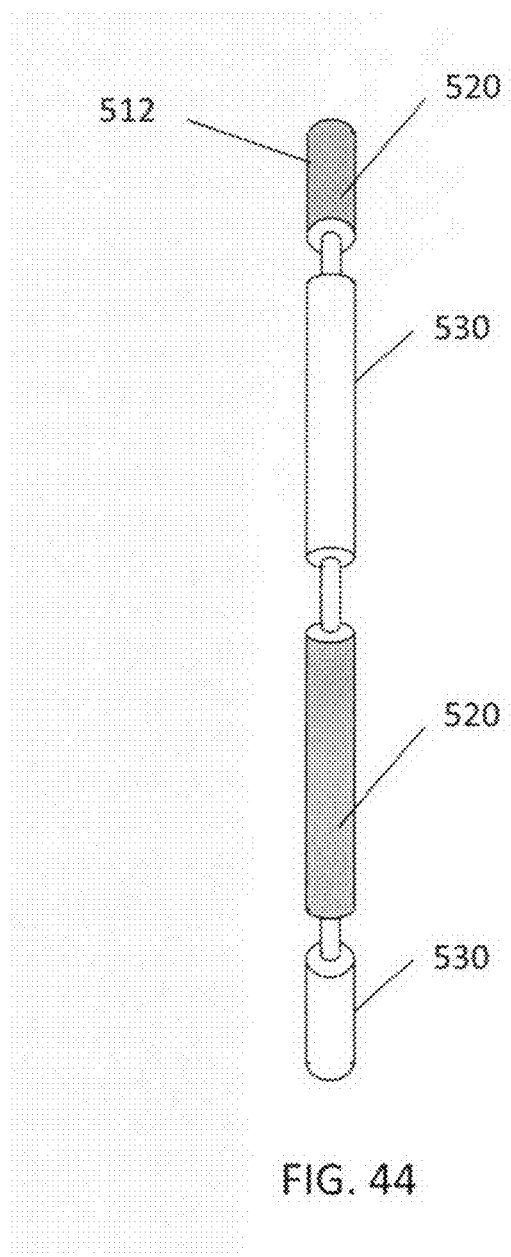

FIG. 43 and FIG. 44 show front and side views of the dental device 512 which is similar to the device 510. The device 512 comprises 4 devices 520 and 4 devices 530. The devices 520 and 530 have different color. FIG. 44 shows that the closed figure of the device 512 is flat. At least containers of the devices 520 and 530 have different colors.

Figure 45:
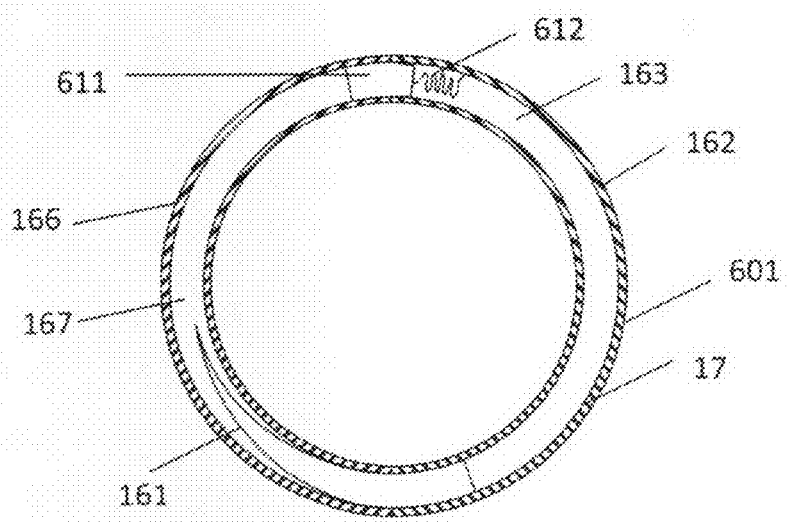

FIG. 45 shows a cross section of the dental device 601. The cleaning part 161 of the dental device 17 is inserted into the cavity 167 of the single piece body 166 and retained sanitary and releasably by the user of the device. The sealing part 611 is partially inserted into to the cavity 167 and affixed to the body 166. The other end of the sealing part 611 is inserted into the cavity 163 of the dental device 17 and retained sanitary and releasably by the user of the device. One end of a length of the dental floss 612 is affixed to the end of the part 611 inserted into the cavity 162. The other end of the dental floss 612 can be affixed to the body 162 inside the cavity 163. The dental device 610 is formed into a closed figure. The cleaning part 161 of the dental device 17 can be released by the user of the device with or without disengagement the 611. The part 611 can be released by the user of the device with or without disengagement the device cleaning part 161. The bodies 162 and 166 can have different colors.

Figure 46:
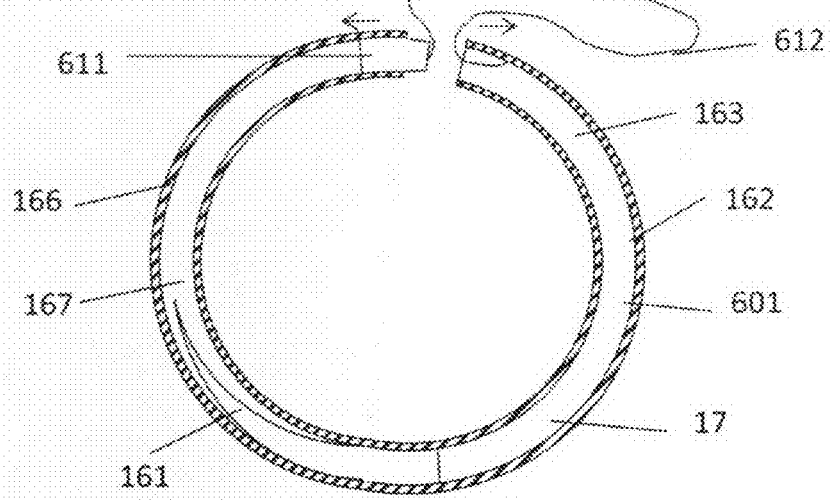
FIGS. 45 and 46 show cross sections of the dental device 601.

FIG. 46 shows a cross section of the dental device 601 with part 611 removed from the cavity 163 and with the released dental floss 612. The cleaning part 161 of the dental device 17 left inserted into the cavity 167.

Figure 47:
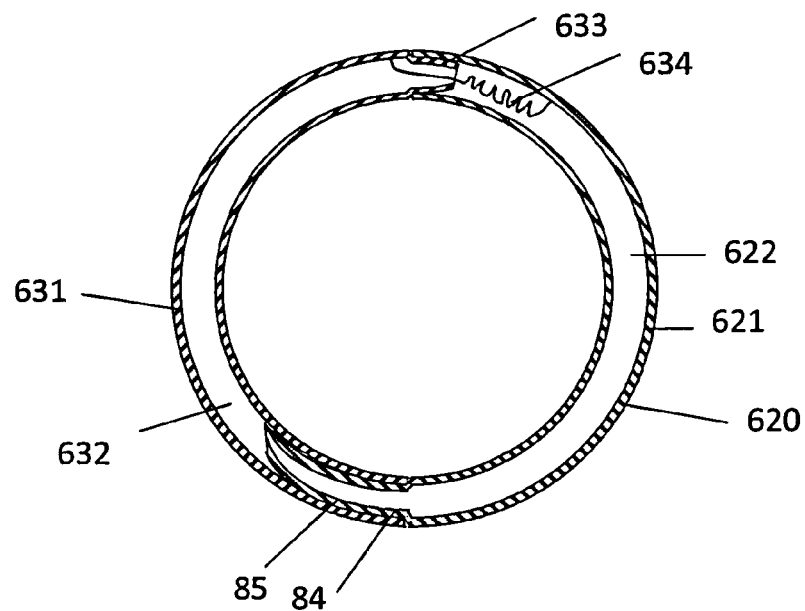
FIGS. 47 and 48 show cross sections of the dental device 620.

FIG. 47 shows a cross section of the dental device 620 comprising a tubular single piece body 621 with a cavity 622 and a tubular single piece body 631 with a cavity 632. The toothpick 84 with an elongated body has the part 85 adapted for cleaning teeth. The cleaning part 85 is shown inserted into the cavity 632 which adapted to receive the cleaning part 85 and retain it sanitary and releasably by the user of the device providing sealing engagement. The sealing part 633 is shown inserted into the cavity 622 which is adapted to receive the sealing part 85 and retain it sanitary and releasably by the user of the device providing sealing engagement. One end of a length of dental floss 634 is affixed to the body 631 inside the cavity 632 and its other end 634 is affixed to the body 621 inside the cavity 622. The dental device 620 is formed into a closed figure. The cleaning part 85 can be released by the user of the device with or without disengagement the part 633. The part 633 and dental floss 634 can be released by the user of the device with or without disengagement the device cleaning part 85. The bodies 621 and 631 can be made bendable, flexible or elastic. They can have different color.

Figure 48:
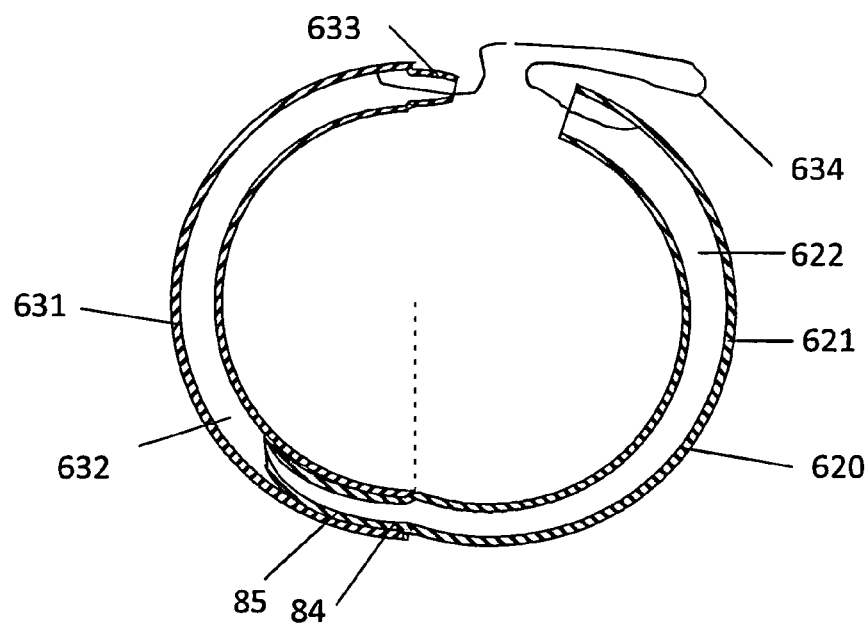

FIG. 48 shows a cross section of the dental device 620 with the part 633 removed from the cavity 622 and the released dental floss 634. The cleaning part 85 is left inserted into the cavity 632.

Figure 49:
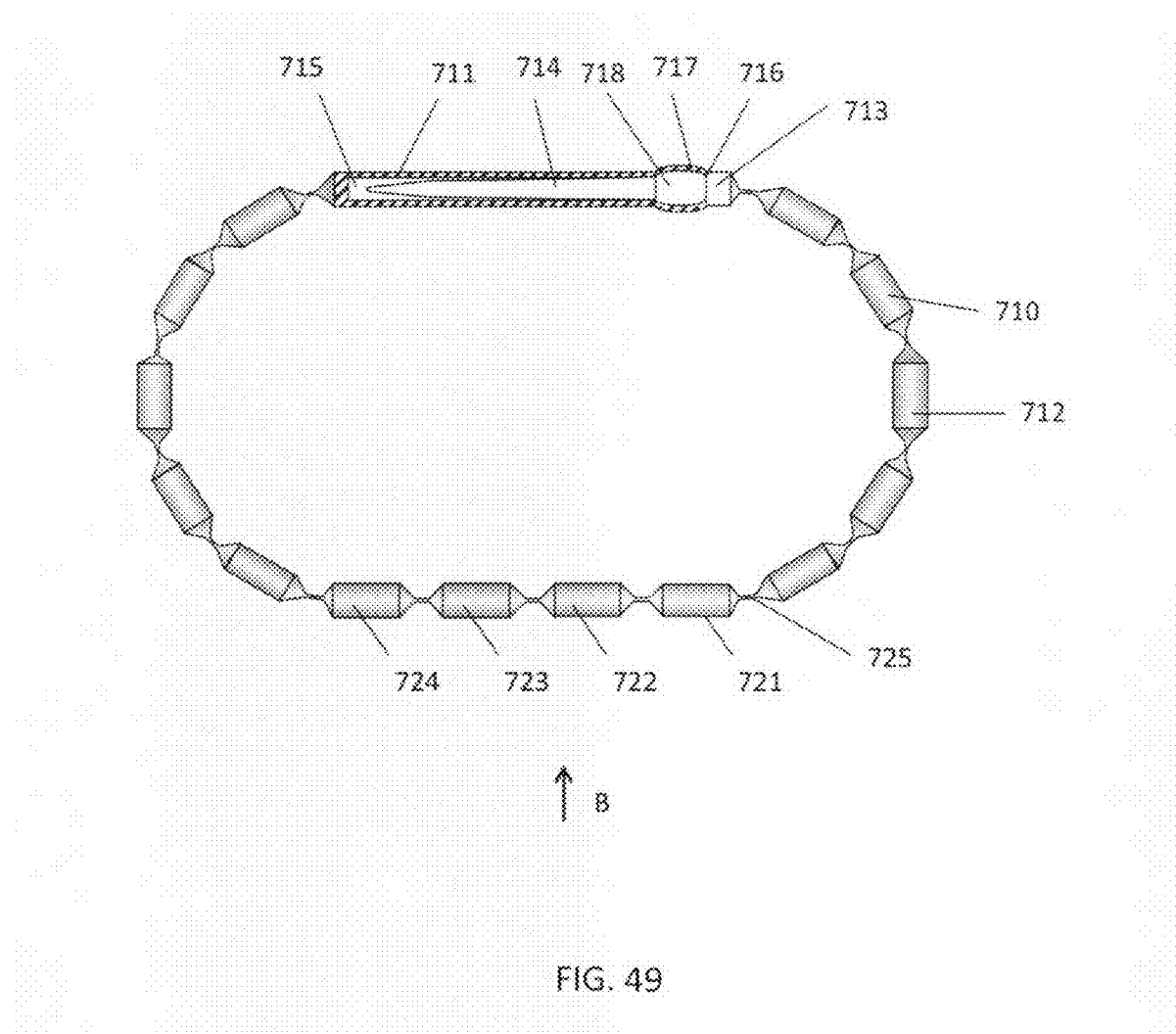
FIG. 49 shows a cross section of the dental device 710.

FIG. 49 shows a cross section of the dental device 710 comprising a container 711, a connector 712 and a toothpick 713 with a cleaning part 714 adapted for cleaning teeth. The whole dental device 710 is made as a single piece body. The container 711 has an internal cavity 715, with the opening 716. The cleaning part 714 is shown inserted into the cavity 715 which is adapted to receive the cleaning part 714 and retain it sanitary and releasably by the user of the device. A part 717 of the container is adapted to snap the part 718 of the toothpick and to provide sealing engagement between them. When the cleaning part 714 of the toothpick 713 is inserted into the cavity 715, the device 710 is formed into a closed figure. The connector has decorative elements, for example, elements 721-724 connected with bendable elements 725. The user of the device can change the shape of the device 710 by bending elements 25. The decorative elements 721-724 can have different colors.

Figure 50:
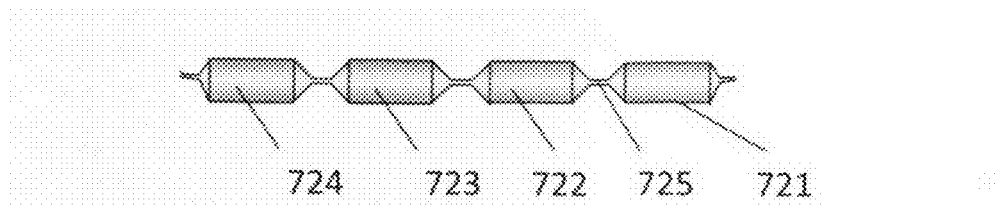
FIG. 50-FIG. 52 show view A on the elements 721-724 formed in different ways.
Figure 51:
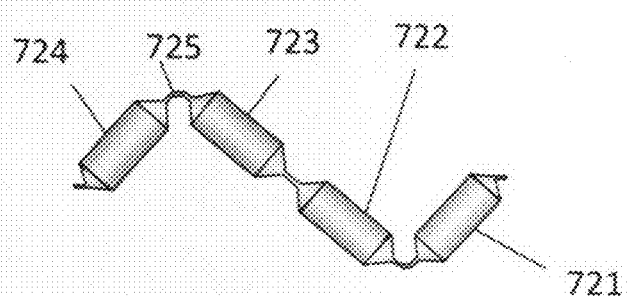
Figure 52:
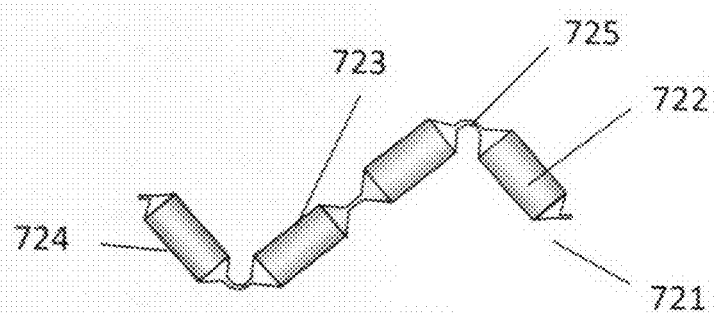

FIG. 50-52 show views B on the elements 721-724 formed in different ways by the user of the device 710. FIG. 50 shows that the elements 721 form a straight line.

FIG. 51 and FIG. 52 show different orientation of the elements 721-724. The device 710 is formed into three-dimensional figure with the shown positioning the elements 721-724. The user of the device can change the shape of the device 710 by bending elements 25.

Figure 53:
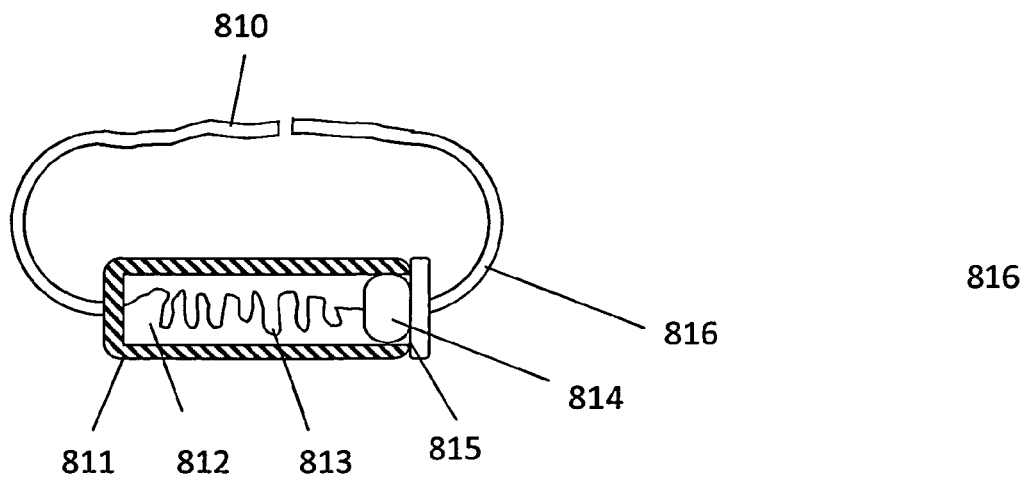
FIGS. 53 and 54 show cross sections of the dental device 810.

FIG. 53 shows a longitudinal cross section cross section of the dental device 810. The dental cleaning device 810 has the length of dental floss 811 attached to the part 812. The part 812 is connected with the connector 813 which is connected with the container 814. The length of dental floss 811 is retained sanitary and releasably by the user of the device in the cavity 815 of the container 814. One end of the floss 811 is affixed to one side of the part 812 adjusted to seal the floss in the cavity 815 and pull it out of the cavity when the floss needed. The other end of the floss can be either affixed to the container 814 inside the cavity 815 or not attached. The connector 813 and the part 812, or the connector 813, the part 812 and the container 814 can be made as a single piece body. When the cavity 815 with the dental floss 811 in it sealed by the part 812, the dental device 810 is formed into a closed figure. The device can be placed around another object, for example a user's wrist of utensils.

Figure 54:
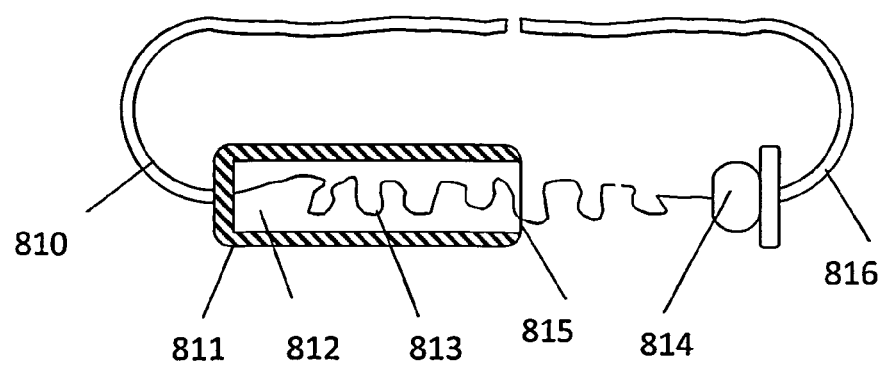

FIG. 54 shows the dental device 810 with the slightly released dental floss 811. The surfaces of the ends of the container 814 and part 812 are smooth and adjusted to prevent any pricking of the user's face or his or her mouth when the dental floss 811 is released and used for cleaning.

The toothpicks, containers and connectors or any of single piece bodies of the invention can be made of bendable, flexible or elastic material. The cleaning part of toothpicks can be made not bendable and adjusted to keep its shape either straight or bent. Material that can be used include nylon, carbon fiber, resins, composites, polymers, and other materials well known to those of skill in the art.

What is claimed is:

1. A dental device for cleaning teeth comprising:
   a) a container having a longitudinal cavity, said container including one closed end with a protruding portion extending therefrom and a bulging open end; an elastic connector having two ends, wherein one end attached to said protruding portion of said closed end;
   b) a bendable toothpick comprising three sections, wherein a first section defining a pointed end adapted for cleaning teeth, a middle section having a bulge portion which is complementary with the shape of said bulging open end, a third section including a diameter being smaller than said middle section, wherein said third section attached to the other end of said elastic connector; said bulge portion of the toothpick releasably snaps into said bulging open end of the container to provide a sealing engagement thus the dental device is formed into a closed configuration; wherein said pointed end of the toothpick positioned within said longitudinal cavity when the device is in closed position.

2. A dental device of claim 1, wherein said elastic connector comprising a plurality of decorative elements.

3. A dental device of claim 2, wherein said decorative elements having different colors.

\* \* \* \* \*